United States Patent
Chovet et al.

(10) Patent No.: US 6,784,208 B2
(45) Date of Patent: *Aug. 31, 2004

(54) METHOD FOR PREVENTING AND TREATING VISCERAL PAIN AND GASTROINTESTINAL DISORDERS

(75) Inventors: Maria Chovet, Montrouge (FR); Laurent Diop, Saclay (FR)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/056,298

(22) Filed: Jan. 25, 2002

(65) Prior Publication Data

US 2002/0161047 A1 Oct. 31, 2002

(30) Foreign Application Priority Data

Jan. 26, 2001 (EP) ............................................. 01400214

(51) Int. Cl.[7] .................... A61K 31/195; A61K 31/185; A61K 31/205
(52) U.S. Cl. ....................... 514/561; 514/553; 514/554; 514/577; 514/578
(58) Field of Search ................................ 514/553, 554, 514/578, 577, 561

(56) References Cited

FOREIGN PATENT DOCUMENTS

| EP | 1031350 | 8/2000 |
|----|---------|--------|
| WO | 9908670 | 2/1999 |
| WO | 9921824 | 5/1999 |
| WO | 0128978 | 4/2001 |

OTHER PUBLICATIONS

Diop et al., "Gabapentin and S–(+)–J–isobutylgaba inhibit the TNBS–induced chronic allodynia in the rat", *Society for Neuroscience Abstracts*, vol. 24, 1998, p. 639.
Diop et al., "Gabapentin and S–(+)–3–isobutylgaba present antihyperalgesic activities in TNBS–induced chronic colonic", *Gastroenterology*, vol. 116, No. 4, part 2, 1999, pp. A896–A897.

Primary Examiner—Shaojia Anna Jiang
(74) Attorney, Agent, or Firm—Charles W. Ashbrook; David R. Kurlandsky

(57) ABSTRACT

The compounds of formula I–IV:

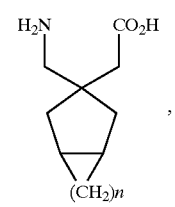

I

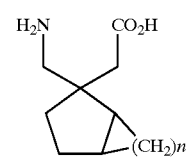

II

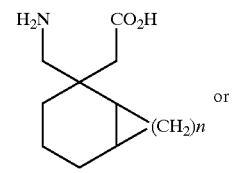

III

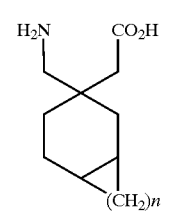

IV wherein n is an integer of from 1 to 4, or pharmaceutically acceptable salts thereof are useful to prevent and treat visceral pain and gastrointestinal disorders.

11 Claims, 1 Drawing Sheet

METHOD FOR PREVENTING AND TREATING VISCERAL PAIN AND GASTROINTESTINAL DISORDERS

This application claims the benefit of European Patent Application No. 01 400 214.1 filed Jan. 26, 2001.

FIELD OF THE INVENTION

This invention relates to a method for preventing and treating visceral pain, and gastrointestinal disorders such as functional bowel disorders and inflammatory bowel diseases, through the use of effective amounts of bicyclic amino acids.

BACKGROUND OF THE INVENTION

The viscera encompasses the organs of the abdominal cavity. These organs include the sex organs, spleen and part of the digestive system. Pain associated with the viscera can be divided into digestive visceral pain and non digestive visceral pain.

Commonly encountered gastrointestinal (GI) disorders include the functional bowel disorders (FBD) and the inflammatory bowel diseases (IBD). These GI disorders include a wide range of disease states that are currently only moderately controlled, including—for FBD, gastro-esophageal reflux, dyspepsia, the irritable bowel syndrome (IBS) and functional abdominal pain syndrome (FAPS), and—for IBD, Crohn's disease, ileitis, and ulcerative colitis, and all regularly produce visceral pain. It has been shown recently in these pathologies, in particular the irritable bowel syndrome and dyspepsia, that the visceral pain threshold is decreased, indicating a visceral hypersensitivity. Other types of visceral pain include the pain associated with dysmenorrhea, pelvic pain, cystitis and pancreatitis.

Few drugs are known to act selectively upon GI disorder-associated hypersensitivity (Farthing M. J. (1998) *Drugs* 56:11–21).

Available treatments of pain fall into two main categories: 1) nonsteroidal anti-inflammatory drugs, used to treat mild pain, but whose therapeutic use is limited by GI adverse effects (gastric erosion, peptic ulcer formation, inflammation of the duodenum and colon); 2) morphine and related opioids, used to treat moderate to severe pain but whose therapeutic use is limited by undesirable side effects including constipation, respiratory depression, tolerance, and abuse potential.

International patent publication WO 99/21824 disclose the use of cyclic amino acids and derivatives thereof for use in treating gastrointestinal disorders such as irritable bowel syndrome.

There is a need for drugs that can alleviate visceral pain without undesirable side effects.

SUMMARY OF THE INVENTION

It has now been found that compounds of formula I–IV (outlined below) are useful for the treatment of disorders such as visceral pain, FBD such as gastro-esophageal reflux, dyspepsia, IBS and FAPS, and IBD such as Crohn's disease, ileitis, and ulcerative colitis, and other types of visceral pain associated with dysmenorrhea, pelvic pain, cystitis and pancreatitis. The inventors have unexpectedly found that the compounds of formula I–IV have the capacity to prevent or treat disorders associated with visceral pain such as:

FBD, including gastro-esophageal reflux, dyspepsia, IBS and FAPS, and

IBD including Crohn's disease, ileitis, and ulcerative colitis, and other types of visceral pain associated with dysmenorrhea, pelvic pain, cystitis and pancreatitis.

This invention provides a method for preventing and treating visceral pain and GI disorders, including FBS and IBD, comprising administering to a subject in need of treatment an effective amount of a compound of formula I–IV:

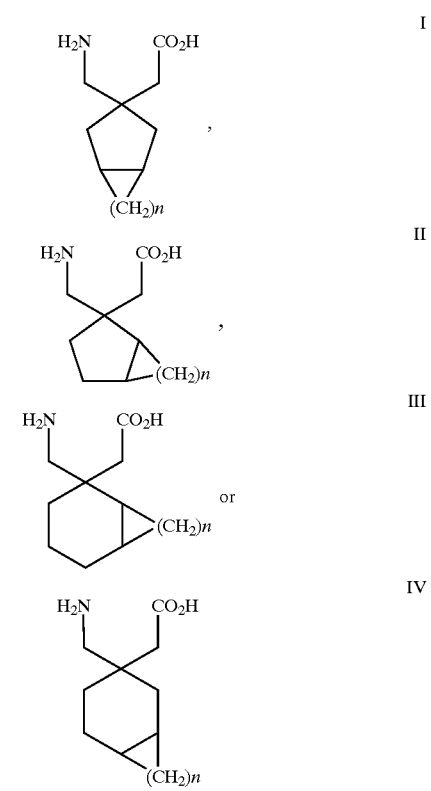

or a pharmaceutically acceptable salt thereof, wherein n is an integer of from 1 to 4. Where there are stereocenters, each center may be independently R or S.

Preferred compounds of the invention are those of formulae I–IV above wherein n is an integer of from 2 to 4.

Other preferred compounds are those of Formula I above.

Especially preferred compounds are:

(1α,6α,8β)(2-Aminomethyl-octahydro-inden-2-yl)-acetic acid, (2-Aminomethyl-octahydro-inden-2-yl)-acetic acid, (2-Aminomethyl-octahydro-pentalen-2-yl)-acetic acid, and (3-Aminomethyl-bicyclo[3.2.0]hept-3-yl)-acetic acid.

A most preferred compound is (1α,3α,5α)-3-aminomethyl-bicyclo[3.2.0]heptane-3-acetic acid, of formula Ia:

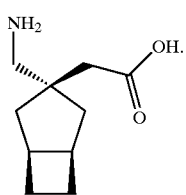

Other preferred compounds are those selected from
(1α,5β)(3-Aminomethyl-bicyclo[3.1.0]hex-3-yl)-acetic acid,
(1α,5β)(3-Aminomethyl-bicyclo[3.2.0]hept-3-yl)-acetic acid,
(1α,5β)(2-Aminomethyl-octahydro-pentalen-2-yl)-acetic acid,
(1α,6β)(2-Aminomethyl-octahydro-inden-2-yl)-acetic acid,
(1α,7β)(2-Aminomethyl-decahydro-azulen-2-yl)-acetic acid,
(1α,5β)(3-Aminomethyl-bicyclo[3.1.0]hex-3-yl)-acetic acid,
(1α,5β)(3-Aminomethyl-bicyclo[3.2.0]hept-3-yl)-acetic acid,
(1α,5β)(2-Aminomethyl-octahydro-pentalen-2-yl)-acetic acid,
(1α,6β)(2-Aminomethyl-octahydro-inden-2-yl)-acetic acid,
(1α,7β)(2-Aminomethyl-decahydro-azulen-2-yl)-acetic acid,
(1α,3α,5α)(3-Aminomethyl-bicyclo[3.1.0]hex-3-yl)-acetic acid,
(1α,3α,5α)(2-Aminomethyl-octahydro-pentalen-2-yl)-acetic acid,
(1α,6α,8α)(2-Aminomethyl-octahydro-inden-2-yl)-acetic acid,
(1α,7α,9α)(2-Aminomethyl-decahydro-azulen-2-yl)-acetic acid,
(1α,3α,5α)(3-Aminomethyl-bicyclo[3.1.0]hex-3-yl)-acetic acid,
(1α,3 β,5α)(3-Aminomethyl-bicyclo[3.2.0]hept-3-yl)-acetic acid,
(1α,3β,5α)(2-Aminomethyl-octahydro-pentalen-2-yl)-acetic acid,
(1α,6α,8β)(2-Aminomethyl-octahydro-inden-2-yl)-acetic acid,
(1α,7α,9β)(2-Aminomethyl-decahydro-azulen-2-yl)-acetic acid,
((1R,3R,6R)-3-Aminomethyl-bicyclo[4.1.0]hept-3-yl)-acetic acid,
((1R,3S,6R)-3-Aminomethyl-bicyclo[4.1.0]hept-3-yl)-acetic acid,
((1S,3S,6S)-3-Aminomethyl-bicyclo[4.1.0]hept-3-yl)-acetic acid,
((1S,3R,6S)-3-Aminomethyl-bicyclo[4.1.0]hept-3-yl)-acetic acid,
((1R,3R,6S)-3-Aminomethyl-bicyclo[4.2.0]oct-3-yl)-acetic acid,
((1R,3S,6S)-3-Aminomethyl-bicyclo[4.2.0]oct-3-yl)-acetic acid,
((1S,3S,6R)-3-Aminomethyl-bicyclo[4.2.0]oct-3-yl)-acetic acid,
((1S,3R,6R)-3-Aminomethyl-bicyelo[4.2.0]oct-3-yl)-acetic acid,
((3αR,5R,7αS)-5-Aminomethyl-octahydro-inden-5-yl)-acetic acid,
((3αR,5S,7αS)-5-Aminomethyl-octahydro-inden-5-yl)-acetic acid,
((3αS,5S,7αR)-5-Aminomethyl-octahydro-inden-5-yl)-acetic acid,
((3αS,5R,7αR)-5-Aminomethyl-octahydro-inden-5-yl)-acetic acid,
((2R,4αS,8αR)-2-Aminomethyl-decahydro-naphthalen-2-yl)-acetic acid,
((2S,4αS,8αR)-2-Aminomethyl-decahydro-naphthalen-2-yl)-acetic acid,
((2S,4αR,8αS)-2-Aminomethyl-decahydro-naphthalen-2-yl)-acetic acid, ((2R,4αR,8αS)-2-Aminomethyl-decahydro-naphthalen-2-yl)-acetic acid,
((2R,4αS,9αR)-2-Aminomethyl-decahydro-benzocyclohepten-2-yl)-acetic acid,
((2S,4αS,9αR)-2-Aminomethyl-decahydro-benzocyclohepten-2-yl)-acetic acid,
((2S,4αR,9αS)-2-Aminomethyl-decahydro-benzocyclohepten-2-yl)-acetic acid,
((2R,4αR,9αS)-2-Aminomethyl-decahydro-benzocyclohepten-2-yl)-acetic acid,
((1R,3R,6S)-3-Aminomethyl-bicyclo[4.1.0]hept-3-yl)-acetic acid,
((1R,3S,6S)-3-Aminomethyl-bicyclo[4.1.0]hept-3-yl)-acetic acid,
((1S,3S,6R)-3-Aminomethyl-bicyclo[4.1.0]hept-3-yl)-acetic acid,
((1S,3R,6R)-3-Aminomethyl-bicyclo[4.1.0]hept-3-yl)-acetic acid,
((1R,3R,6R)-3-Aminomethyl-bicyclo[4.2.0]oct-3-yl)-acetic acid,
((1R,3S,6R)-3-Aminomethyl-bicyclo[4.2.0]oct-3-yl)-acetic acid,
((1S,3S,6S)-3-Aminomethyl-bicyclo[4.2.0]oct-3-yl)-acetic acid,
((1S,3R,6S)-3-Aminomethyl-bicyclo[4.2.0]oct-3-yl)-acetic acid,
((3α,5R,7αR)-5-Aminomethyl-octahydro-inden-5-yl)-acetic acid,
((3αR,5S,7αR)-5-Aminomethyl-octahydro-inden-5-yl)-acetic acid,
((3αS,5S,7αS)-5-Aminomethyl-octahydro-inden-5-yl)-acetic acid,
((3αS,5R,7αS)-5-Aminomethyl-octahydro-inden-5-yl)-acetic acid,
((2R,4αR,8αR)-2-Aminomethyl-dctahydro-naphthalen-2-yl)-acetic acid,
((2S,4αS,8αR)-2-Aminomethyl-decahydro-naphthalen-5-2-yl)-acetic acid,
((2S,4αR,8αS)-2-Aminomethyl-decahydro-naphthalen-5-2-yl)-acetic acid,
((2R,4αS,8αS)-2-Aminomethyl-decahydro-naphthalen-2-yl)-acetic acid,
((2R,4αR,9αR)-2-Aminomethyl-decahydro-bentzocyclohepten-2-yl)-acetic acid,
((2R,4αR,9αR)-2-Aminomethyl-decahydro-benzocyclohepten-2-yl)-acetic acid,
((2S,4αS,9αS)-2-Aminomethyl-decahydro-benzocyclohepten-2-yl)-acetic acid, and ((2R,4αS,9αS)-2-Aminomethyl-decahydro-benzocyclohepten-2-yl)-acetic acid.

This invention also concerns the use of a compound of formula I–IV for the preparation of a medicament useful for preventing or treating visceral pain and gastrointestinal disorders such as:

FBD including gastro-esophageal reflux, dyspepsia, IBS, FAPS, and

IBD including Crohn's disease, ileitis, and ulcerative colitis, other types of visceral pain associated with dysmenorrhea, pelvic pain, cystitis and pancreatitis, in particular by the oral route.

DETAILED DESCRIPTION OF THE INVENTION

Figure 1:
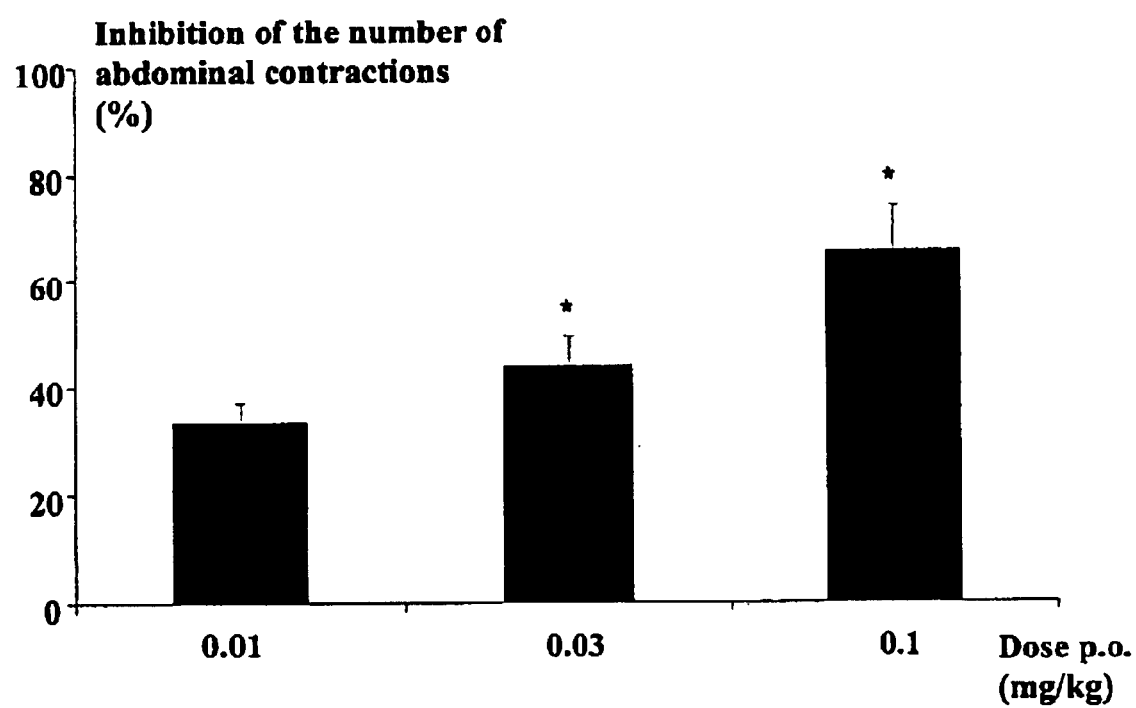
FIG. 1: Dose response curve of the compound of formula Ia on LPS-induced rectal hyperalgesia. *=p<0.05

The inventors have shown that compounds of formula I–IV are effective for the treatment of visceral pain, when administered orally. One pharmacological model used is a model of TNBS-induced chronic visceral pain in rats (Diop L. et al, *Gastroenterology* 1999, 116, 4(2): A986). More particularly, the inventors have surprisingly shown that the compound of formula Ia is 20 fold more effective than gabapentin for the treatment of viscerial pain in the TNBS-induced chronic visceral pain model.

Moreover, in an LPS-induced rectal hypersensitivity model of visceral pain in rats (Eutamene H et al, *J Pharmacol Exp Ther* 2000 295 (1):162–7), the compound of formula Ia was shown to be effective at treating visceral pain. In this model the compound was shown to be about 500 fold more potent than gabapentin for the treatment of visceral pain.

The compound of Formula I–IV may be utilized as a solvate, hydrate, pharmaceutically acceptable salt, or a polymorph (different crystalline lattice descriptors).

Since amino acids are amphoteric, pharmacologically compatible salts can be salts of appropriate inorganic or organic acids, for example, hydrochloric, sulphuric, phosphoric, acetic, oxalic, lactic, citric, malic, salicylic, malonic, maleic, succinic, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethyl-ammonium ion. (See also "Pharmaceutical salts" by Berge S. M. et al. (1997) *J. Pharm. Sci.* 66: 1–19, which is incorporated herein by reference.)

Prodrugs of the compound of formula I-TV are included in the scope of the instant invention. Aminoacyl-glycolic and lactic esters are known as prodrugs of amino acids (Wermuth C. G., *Chemistry and Industry,* 1980:433–435). The carbonyl group of the amino acids can be esterified by known means. Prodrugs and soft drugs are known in the art (Palomino E., *Drugs of the Future,* 1990;15(4):361–368). The last two citations are hereby incorporated by reference.

The effectiveness of an orally administered drug is dependent upon the drug's efficient transport across the mucosal epithelium and its stability in entero-hepatic circulation. Drugs that are effective after parenteral administration but less effective orally, or whose plasma half-life is considered too short, may be chemically modified into a prodrug form.

A prodrug is a drug which has been chemically modified and may be biologically inactive at its site of action, but which may be degraded or modified by one or more enzymatic or other in vivo processes to the bioactive form.

This chemically modified drug, or prodrug, should have a different pharmacokinetic profile to the parent, enabling easier absorption across the mucosal epithelium, better salt formulation and/or solubility, improved systemic stability (for an increase in plasma half-life, for example). These chemical modifications may be 1) ester or amide derivatives which may be cleaved by, for example, esterases or lipases. For ester derivatives, the ester is derived from the carboxylic acid moiety of the drug molecule by known means. For amide derivatives, the amide may be derived from the carboxylic acid moiety or the amine moiety of the drug molecule by known means.

2) peptides which may be recognized by specific or non-specific proteinases.

A peptide may be coupled to the drug molecule via amide bond formation with the amine or carboxylic acid moiety of the drug molecule by known means.

3) derivatives that accumulate at a site of action through membrane selection of a prodrug form or modified prodrug form, 4) any combination of 1) to 3).

Current research in animal experiments has shown that the oral absorption of certain drugs may be increased by the preparation of "soft" quaternary salts. The quaternary salt is termed a "soft" quaternary salt since, unlike normal quaternary salts, e.g., $R-N^+(CH_3)_3$, it can release the active drug on hydrolysis.

"Soft" quaternary salts have useful physical properties compared with the basic drug or its salts. Water solubility may be increased compared with other salts, such as the hydrochloride, but more important there may be an increased absorption of the drug from the intestine. Increased absorption is probably due to the fact that the "soft" quaternary salt has surfactant properties and is capable of forming micelles and unionized ion pairs with bile acids, etc., which are able to penetrate the intestinal epithelium more effectively. The prodrug, after absorption, is rapidly hydrolyzed with release of the active parent drug.

The compounds of the present invention can exist in an unsolvated form or solvated form, including a hydrated form. In general, the solvated forms, are equivalent to unsolvated form and are intended to be encompassed within the scope of the present invention.

The term "patient" is intended to include a mammal, especially a human.

All that is required to practice the method of preventing and treating visceral pain and GI disorders such as FBD or IBD according to the present invention is to administer a compound of formula I–IV in an amount that is effective to prevent or treat the damaged condition, i.e. to control visceral pain and/or FBD or IBD. The effective amount of a compound of formula I–IV to be utilized will generally be from about 1 to about 300 mg/kg of patient body weight. Typical doses will be from about 10 to about 5000 mg per day for an adult patient of normal weight.

Typical FBD conditions include gastro-esophageal reflux disease, dyspepsia, and IBS and FAPS.

Typical IBD conditions include ileitis, ulcerative colitis, and Crohn's disease.

Other visceral pain disorders include the pain associated with dysmenorrhea, cystitis, pelvic pain and pancreatitis.

In a further aspect of the present invention, there is provided a pharmaceutical composition for the treatment or prevention of visceral pain and GI disorders comprising the active component, of a compound of formula I–IV. Pharmaceutical compositions of the compound of the present invention—including one of its salts, are produced by formulating this active component in dosage unit form with at least one pharmaceutically acceptable carrier or excipient. For preparing pharmaceutical compositions from the compound used in this invention, inert, pharmaceutically acceptable carriers can be either solid or liquid.

Solid dosage forms for oral administration include capsules, tablets, pills, powders, and granules. They preferably contain about 5% to about 70% of a compound of formula I–IV. In such solid dosage forms, the active component is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alginates, gelatin, polyvinylpyrrolidone, sucrose, and acacia, (c) humectants, as for example, glycerol, (d) disintegrating agents, as for example, agar—agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose as well as high molecular weight polyethyleneglycols, and the like.

Solid dosage forms such as tablets, dragées, capsules, pills, and granules can be prepared with coatings and shells, such as enteric coatings and others well known in the art. They can also be of such composition that they release the active component in a certain part of the intestinal tract in a delayed manner. Examples of embedding compositions which can be used are polymeric substances and waxes. The active component can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to a compound of formula I–IV, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, and the like.

Suspensions, in addition to the active component, may contain suspending agents, as for example, ethoxylated isostearyl alcohols, polyoxyethylene sorbitol and sorbitan esters, microcrystalline cellulose, aluminum metahydroxide, bentonite, agar—agar and tragacanth, or mixtures of these substances, and the like.

Compositions for rectal administrations are preferably suppositories which can be prepared by mixing the compound of the present invention with suitable non-irritating excipients or carriers such as cocoa butter, polyethyleneglycol or a suppository wax, which are solid at ordinary temperatures but liquid at body temperature, and therefore melt in the rectum and release the active component.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable liquid carriers, diluents, solvents or vehicles include water, ethanol, polyols (propyleneglycol, polyethyleneglycol, glycerol, and the like), and suitable mixtures thereof.

These compositions may also contain adjuvants such as preserving, wetting, emulsifying, and dispersing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like.

Preferably the pharmaceutical preparation is in unit dosage form. In such form, the preparation is divided into unit doses containing appropriate quantities of a compound of formula I–IV. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms. Some examples of dosage unit forms are tablets, capsules, pills, powders, suppositories, aqueous and nonaqueous oral solutions and suspensions, and parenteral solutions packaged in containers containing either one or some larger number of dosage units and capable of being subdivided into individual doses.

The percentage of the active component in the foregoing compositions can be varied within wide limits, but for practical purposes it is preferably present in a concentration of at least 10% in a solid composition and at least 2% in a primary liquid composition. The most satisfactory compositions are those in which a much higher proportion of the active component is present, for example, from 10% to 90% by weight.

Routes of administration of compounds of formula I–IV, or their salts are parenteral preferably oral, or by enema. For example, a useful oral dosage is between 1 mg and 1 g, preferably between 20 mg and 800 mg, and a useful intravenous dose is between 0.1 mg and 1 g, more preferably between 5 mg and 50 mg. The dosage is within the dosing range used in treatment of visceral pain and GI disorders such as FBD or IBD, or as would be dictated by the needs of the patient as described by the physician.

A unit dosage form of a compound of formula I–IV to be used in this invention may also comprise other compounds useful in the therapy of visceral pain and GI disorders.

The advantages of using a compound of formula I–IV in the instant invention include the selective activity of the compound on visceral pain, the relatively nontoxic nature of the compound, the ease of preparation, the fact that the compound is well tolerated, and the ease of i.v. and, in particular, oral administration of the drug.

EXAMPLES

The methods of synthesis of the compounds of formula I-TV are described below by way of examples 1–9. Biological examples are shown by way of examples 10 and 11.

Synthesis Examples

Example 1
(±)-(1α,6β)(2-Aminomethyl-octahydro-inden-2-yl)-acetic Acid Hydrochloride

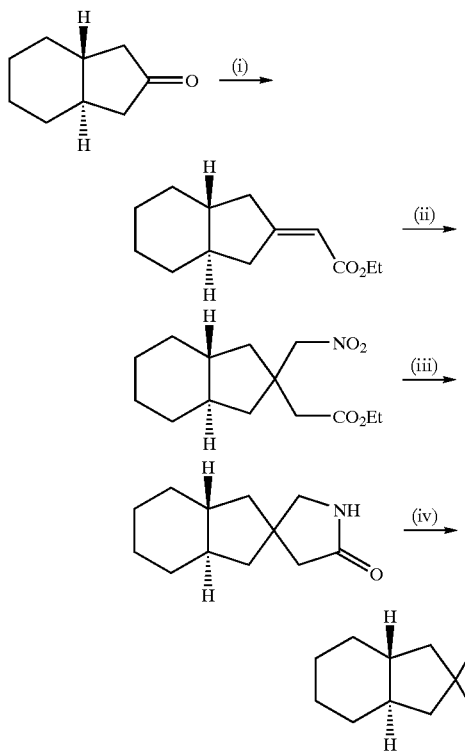

Step (i)

Sodium hydride (0.11 mg, 2.7 mmol) was stirred with THF (5 mL) at 0° C. under argon. Triethylphosphonoacetate (0.5 mL) was added dropwise and the solution stirred for 10 minutes. The ketone (0.37 g, 7.7 mmol) in THF (5 mL) was added dropwise with stirring and left to warm to room temperature. After 18 hours, the reaction mixture was separated between water (80 mL) and diethyl ether (3×20 mL). Solvent was removed in vacuo to give a yellow oil, which was purified via flash chromatography (silica, heptane/EtOAC 19:1). To give 0.34 g (62%) of the ester as a colorless oil:

$^1$H NMR (CDCl$_3$) (400 MHz): 1.05–1.29 (9H, m, ring protons +CH$_3$), 1.76–1.78 (2H, m, ring protons), 1.87–1.97 (2H, m, ring protons), 2.0–2.16 (2H, m, ring protons), 2.51–2.56 (1H, dd, J=5.7, 27.5 Hz, ring protons), 3.12–3.18 (1H, dd, J=5.4, 18.8 Hz, ring protons), 4.12–4.20 (2H, m, CH$_2$), 5.77 (1H, s, CH).

MS (ES$^+$) m/e 209 [M+H]$^+$100%.

Step (ii)

Ester (0.34 g, 1.63 mmol) was dissolved in THF (5 mL), with stirring under argon. Nitromethane (0.25 mL) was added and the reaction mixture heated to 60° C. TBAF (2.3 mL) was added dropwise to the hot solution over 1 hour and stirred for 4 hours. The reaction mixture was partitioned between 2N HCl and diethyl ether, and the diethyl ether layer was washed with brine. Solvent was removed in vacuo to give a yellow oil, which was purified via flash chromatography (silica, heptane/EtOAC, 19:1), to give 0.264 g (60%) of the product as a colorless oil.

$^1$H NMR (CDCl$_3$) (400 MHz): δ0.97–1.30 (11H, m, ring protons +CH$_3$), 1.73–1.95 (6H, m, 2×CH+4 ring protons), 2.5 (1H, d, J=16.6 Hz, CH$_2$CO$_2$Et), 2.7 (1H, d, J=16.6 Hz, CH$_2$CO$_2$Et), 4.12–4.18 (2H, m CH$_2$), 4.49–4.51 (1H, d, J=11.5 Hz, CH$_2$NO$_2$), 4.73–4.75 (1H, d, J=11.5 Hz, CH$_2$NO$_2$).

Step (iii)

Nitroester (0.24 g, 0.9 mmol) was dissolved in methanol with Nickel sponge. Reaction was hydrogenated at 50 psi, 30° C. for 15 hours. The reaction mixture was filtered through celite, and the solvent removed in vacuo to give the product 0.18 g (85%) as a yellow solid. This product was a mixture of lactam and amino ester.

Step (iv)

Amino ester was taken up in 6N HCl (5 mL) and dioxane (2.5 mL), and heated to reflux for 4 hours. The solution was washed with dichloromethane (3×5 mL), and the aqueous fraction was evaporated in vacuo to give 0.196 g (99%) of product as a colorless solid.

$^1$H NMR (DMSO) (400 MHz): δ0.86–1.04 (2H, m), 1.08–1.17 (6H, m), 1.60–1.78 (6H, m), 2.35–2.39 (1H, d, J=16 Hz, CH$_2$CO$_2$H), 2.46 (1H, m, CH$_2$CO$_2$H), 2.83–2.87 (1H, d, J=13 Hz, CH$_2$NH$_2$), 2.97–3.00 (1H, d, J=13 Hz, CH$_2$NH$_2$), 7.91 (2H, bs, NH$_2$)

MS (ES+) m/e 212 [M+H]+100%.

HPLC, Prodigy C18 column, 5% methanol/acetonitrile. Retention time=3.00 minutes, and a purity of 99%.

Example 2
(±)-(1α,5β)(2-Aminomethyl-octahydro-pentalen-2-yl)-acetic acid hydrochloride

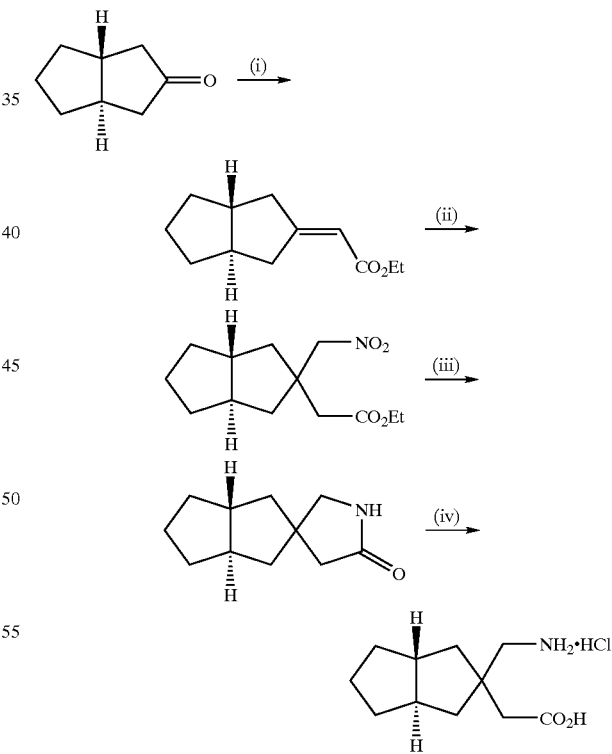

Step (i)

Sodium hydride (0.6 g, 14.5 mmol) was stirred with THF (50 mL) at 0° C. under argon. Triethylphosphonoacetate (2.9 mL) was added dropwise and the solution stirred for 10 minutes. The ketone (1.8 g, 14.5 mmol) in THF (10 mL) was added dropwise with stirring and left to warm to room temperature. After 18 hours, the reaction mixture was separated between water (250 mL) and diethyl ether (3×50 mL). Solvent was removed in vacuo to give a yellow oil, which was purified via flash chromatography (silica, heptane/EtOAC 19:1). To give 1.95 g (69%) of the ester was a colorless oil:

$^1$H NMR (CDCl$_3$) (400 MHz): δ1.14–1.19 (2H, m, CH$_2$), 1.25–1.29 (3H, m, CH$_3$), 1.55–1.79 (4H, m, 2×CH$_2$), 2.03–2.10 (4H, m, 2×CH$_2$), 2.45–2.55 (1H, dd, CH), 3.05–3.15 (1H, dd, CH), 4.12–4.17 (2H, q, J=7.3, 14.4 Hz, COCH$_2$), 5.76 (1H, m, CH).

Step (ii)

Ester (1.9 g, 10 mmol) was dissolved in THF (15 mL), with stirring under argon. Nitromethane (1.4 mL) was added, and the reaction mixture heated to 60° C. TBAF (14 mL) was added dropwise to the hot solution over 1 hour, and stirred for 5 hours. The reaction mixture was separated between 2N HC 1 and diethyl ether, and then the ether layer was washed with brine. Diethyl ether was removed in vacuo to give an orange oil, which was purified via flash chromatography (silica, heptane/EtOAC, 19:1), to give 1.59 g (64%) of the product as a colorless oil.

1H NMR (CDCl$_3$) (400 MHz): δ1.14–1.31 (7H, m, CH$_3$+ ring protons), 1.64–1.72 (5H, m, ring protons), 1.03–1.09 (1H, m, ring protons), 2.00–2.05 (2H, m, ring protons), 2.57–2.61 (1H, d, J=16.4 Hz, CH$_2$CO$_2$Et), 2.71–2.75 (1H, d, J=16.4 Hz, CH$_2$CO$_2$Et), 4.12–4.18 (2H, q, J=7.1, 14.2 Hz, OCH$_2$CH$_3$), 4.56–4.59 (1H, d, J=11.5 Hz, CH$_2$NO$_2$), 4.77–4.80 (1H, d, J=11.5 Hz, CH$_2$NO$_2$) IR (neat)2957, 2870, 1731, 1547, 1374, 1182, 1030 cm$^{-1}$.

Step (iii)

Nitroester (1.59 g, 5.9 mmol) was dissolved in methanol (40 mL) with Nickel sponge. Reaction was hydrogenated at 50 psi, 30° C. for 5 hours. The reaction mixture was filtered through celite, and the solvent removed in vacuo to give the lactam 1.08 g (97%) as an off-white solid.

$^1$H NMR (CDCl$_3$) (400 MHz): δ1.08–1.11 (2H, m, ring protons), 1.23–1.28 (2H, m, ring protons), 1.62–1.68 (4H, m), 1.82–1.89 (2H, m), 2.00–2.06 (2H, m), 2.30–2.40 (2H, m, CH$_2$CO), 3.29–3.30 (2H, M, CH$_2$NH), 5.45 (1H, bs, NH).

MS (ES$^+$) m/e 180[M+H]$^+$3%, 359 [2M+H]$^+$21%, 381 [2M+Na]$^+$100%.

Step (iv)

Lactam was taken up in 6N HCl (20 mL) and dioxane (8 mL), and heated to reflux for 4 hours. The solution was washed with dichloromethane (3×10 mL), and the aqueous fraction was evaporated in vacuo to give 0.65 g (84%) of product as a colorless solid.

$^1$H NMR (DMSO) (400 MHz): δ1.0–1.18 (4H, m, ring protons), 1.52–1.72 (6H, m, ring protons), 1.95–2.02 (2H, m, ring protons), 2.33–2.67 (2H, m, CH$_2$CO$_2$H), 2.90–2.94 (1H, d, J=12.9 Hz, CH$_2$NH$_2$), 3.00–3.03 (1H, d, J=12.7 Hz, CH$_2$NH$_2$), 7.94 (2H, bs, NH$_2$).

MS (ES$^+$) m/e 198 [M+H]$^+$100%.

LCMS (ELSD) Prodigy ODS3 50 mm×2 mm column, 5%–50% MeCN/H$_2$O.

Retention time=2.30 minutes, mass found=198. 100% purity.

Example 3
(1α,3α,5α)(2-Aminomethyl-octahydro-pentalen-2-yl)-acetic acid hydrochloride

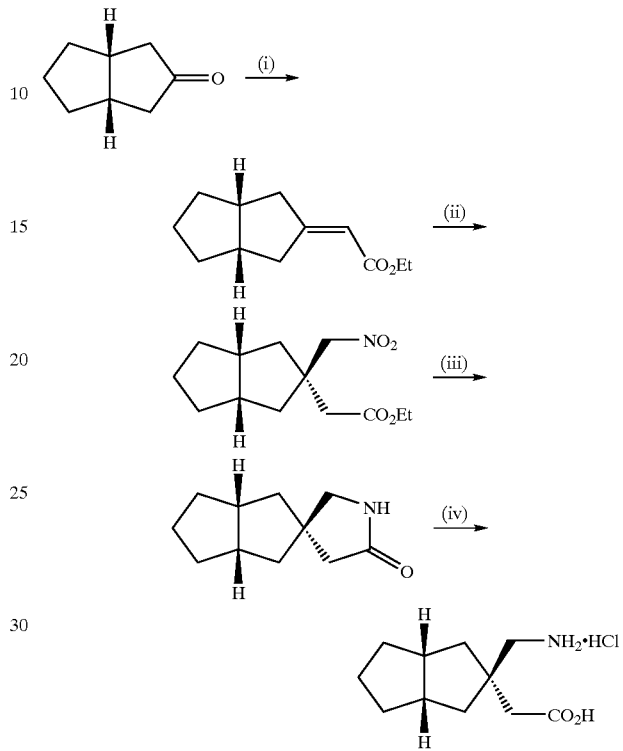

Step (i)

To a suspension of NaH (0.45 g, 11.3 mmol) in THF (25 mL), at 0° C. under argon, was slowly added (over 10 minutes) triethylphosphonoacetate (2.3 mL, 11.6 mmol), followed by 5 (1.29 g, 10.4 mmol in 2×3 mL THF). The reaction was allowed to warm to room temperature and left to stir for 4 hours, after which it was diluted with water (100 mL), extracted with ether (2×200 mL), washed with saturated brine (50 mL), and dried (MgSO$_4$). Column chromatography (9:1 heptane/ethyl acetate) gave the product as a colorless oil, 1.75 g, 86%.

IR (thin film) (cm$^{-1}$) v=2964, 1713, 1655, 1371, 1208, 1125, 1040.

$^1$H NMR (CDCl$_3$): δ5.72 (1H, m), 4.14 (2H, q, J=7.2), 3.02–2.92 (1H, m), 2.72–2.54 (3H, m), 2.52–2.42 (1H, m), 2.28–2.20 (1H, m), 1.85–1.31 (6H, m), 1.27 (3H, t, J=7.2).

m/z AP$^+$195 (MI+1) at 100%.

Step (ii)

To a solution of 6 (2.75 g, 22.2 mmol) in THF (22 mL) was added TBAF (24 mL, 24.0 mmol) followed by nitromethane (4.4 mL, 8.14 mmol). The reaction was heated (oil bath at 60° C.) for 4.75 hours, after which it was diluted with ethyl acetate (100 mL) and washed with 2M HCl (30 mL), followed by saturated brine (40 mL), dried (MgSO$_4$), and concentrated under reduced pressure. Column chromatography (9:1 heptane/ethyl acetate) gave the product as a colorless oil, 0.73 g, 20%. The product was found by $^1$H NMR to be a 9:1 mixture of diastereoisomers.

$^1$H NMR (CDCl$_3$): δ4.67 (1H, s), 4.60 (1H, s), 4.15 (2H, q, J=7.2), 4.14 (2H, q, 7.2), 2.58 (2H, s), 2.49 (2H, s), 2.12–2.0 (2H+2H, m), 1.63–1.49 (4H+4H, m), 1.44–1.36 (2H+2H, m) 1.28 (3H, t, J=7.2), 1.27 (3H, t, J=7) 1.16–1.04 (2H+2H, m).

Step (iii)

Compound 7 (0.88 g, 3.45 mmol) in methanol (100 mL) with nickel sponge catalyst underwent hydrogenation at 30° C. and a pressure of 56 psi; this was left for 5 hours. Before use, the nickel sponge catalyst was washed several times, first with water and then methanol. After hydrogenation was complete, the reaction mixture was filtered through celite and the resulting solution concentrated in vacuo to give a yellow solid, 0.62 g, 80%.

$^1$H NMR (CDCl$_3$): δ5.43 (1H, br s), 3.15 (2H, s), 2.56–2.44 (3H, m), 1.99 (2H, dd, J=12.6, 8.2), 1.64–1.50 (2H, m), 1.44–1.34 (3H, m), 1.22–1.14 (2H, m). m/z ES+226 (MI+1) at 100%.

Step (iv)

Compound 8 (0.61 g, 2.7 mmol) in dioxane (10 mL) and 6 M HC 1 (30 mL) was heated to reflux (oil bath at 100° C.) for 4 hours. After cooling, the reaction was diluted with water (40 mL) and the reaction mixture washed with dichloromethane (3×40 mL) and concentrated in vacuo to yield a white crystalline product as a 6:1 ratio of diastereoisomers. The product was recrystallized twice from ethyl acetate/methanol to give a 10:1 mixture of diastereoisomers.

m/z ES$^+$198 (MI+1) at 100%.

$^1$H NMR (D$_2$O): δ3.03 (2H, s), 2.50–2.36 (4H, m), 1.84 (2H, dd, J=12, 8), 1.41 (4H, s), 1.26 (2H, s), 1.02 (2H, m). HPLC column=Prodigy ODS 3, room temperature=0.87, Purity=100%.

Example 4

(1α,6α,8α)(2-Aminomethyl-octahydro-inden-2-yl)-acetic acid hydrochloride

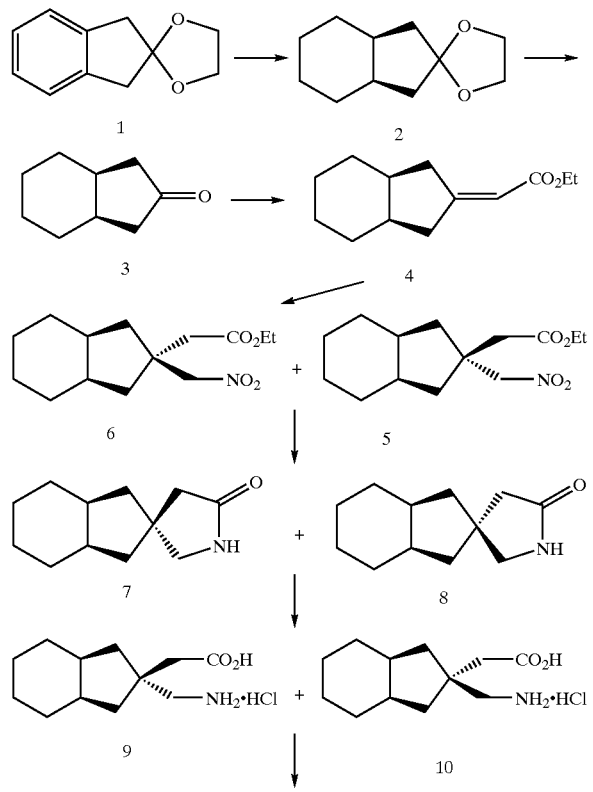

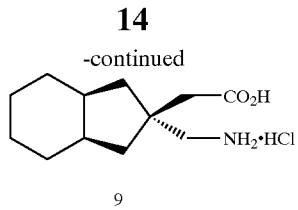

Synthesis of Compound 1

Indan-2-one (1.0 g, 7.6 mmol), ethylene glycol (0.43 mL, 7.6 mmol), and para-toluene sulphonic acid were refluxed in benzene (40 mL) using a Dean-Stark trap for 6 hours. The mixture was allowed to cool and was then diluted with ethyl acetate (100 mL) and washed with saturated sodium hydrogen carbonate solution (60 mL). The organic layer was separated off, and the aqueous layer was extracted further with ethyl acetate (2×50 mL). The combined organic fractions were washed with brine, dried (MgSO$_4$), and the solvent was evaporated under reduced pressure. The residue was chromatographed (SiO$_2$, heptane/ethyl acetate, 97:3) to give the acetal 1 (1.14 g, 85%) as a colorless oil; Rf (heptane/ethyl acetate, 8:2) 0.36; $v_{max}$(film)/cm$^{-1}$ 1483, 1331, 1291, 1105; δH ($^{400}$MHz; CDCl$_3$): 7.19–7.14 (4H, m, Ph), 4.02 (4H, s, 2×CH$_2$CO$_2$), 3.18 (4H, s, 2×CH$_2$O).

Synthesis of Compound 2

Acetal 1 (0.5 g, 2.84 mmol) in ethanol (50 mL) was shaken over a catalytic amount of 5% rhodium on alumina under a hydrogen atmosphere (70 Psi, 50° C.) for 16 hours. The catalyst was filtered off, and the solvent was evaporated under reduced pressure to give the acetal 2 (0.51 g, 99%) as a colorless oil; $v_{max}$(film)/cm$^{-1}$ 2923, 1449, 1337, 1192, 1115, 1089; δH (400 MHz; CDCl$_3$): 3.89–3.86 (4H, m, 2×CH$_2$O), 2.10–2.00 (2H, m), 1.88 (2H, dd,J=13.9,7.6), 1.81 (2H, dd, J=13.7, 7.0), 1.56–1.26 (6H, m).

Synthesis of Compound 3

Acetal 2 (1.01 g, 5.54 mmol) was stirred in a mixture of 2N hydrochloric acid (10 mL) and acetone (10 mL) for 24 hours. After this time, tlc showed complete consumption of the starting acetal. Saturated sodium carbonate solution (20 mL) was added, and the mixture was extracted with ether (3×25 mL). The combined ether fractions were washed with brine, dried (MgSO$_4$), and the solvent was evaporated under reduced pressure. The residue was chromatographed (SiO$_2$, pentane/ether, 95:5) to give the ketone 3 (0.75 g, 97%) as a colorless oil; R$_f$(heptane/ethyl acetate, 8:2) 0.42; $v_{max}$(film)/cm$^{-1}$ 1743 (C=O); δ$_H$ (400 MHz; CDCl$_3$): 2.37–2.28 (2H, m), 2.20 (2H, dd, J=18.5, 7.5), 2.12 (2H, dd, J=18.7, 6.3), 1.65–1.24 (10H, m).

Synthesis of Compound 4

Triethyl phosphonoacetate (1.13 mL, 5.70 mmol) was added dropwise to a stirring suspension of sodium hydride (0.22 g of a 60% dispersion in oil, 5.43 mmol) in THF (15 mL) at 0° C. under argon. After 20 minutes, ketone 3 (0.75 g, 5.43 mmol) in THF (6 mL) was added dropwise. The mixture was allowed to warm to room temperature and stirred for 16 hours. Water (5 mL) was added, and the mixture was extracted with ether (15 mL×3). The combined organic fractions were washed with brine and dried (MgSO$_4$). The solvent was evaporated under reduced pressure. The residue was chromatographed (SiO$_2$, heptane/ethyl acetate, 95:5) to give the ester 4 (0.81 g, 72%) as a colorless oil; R$_f$(heptane/ethyl acetate, 8:2) 0.66; $v_{max}$(film)/cm$^{-1}$ 1715 (C=O), 1652 (C=C); δ$_H$ (400 MHz; CDCl$_3$): 5.80 (1H, quin, J=2.2, CHCO$_2$Et), 4.15 (2H, q, J=7.1, CO$_2$CH$_2$Me), 2.79 (1H, dd, J=19.5, 8.1), 2.69 (1H, ddt, J=19.8, 7.3, 2.3), 2.47 (1H, dd, J=17.3, 7.2), 2.34 (1H, ddt, J=17.3, 5.6, 1.8), 2.14 (1H, m), 2.02 (1H, m), 1.60–1.22 (8H, m); m/z (ES$^+$) 209 (M+H, 57%), 455 (2M+K, 67).

Synthesis of Compounds 5 and 6

Ester 4 (0.45 g, 2.16 mmol), nitromethane (0.24 mL, 4.31 mmol), and tetra-butylammonium fluoride (3.10 mmol of a 1 M solution in THF, 3.10 mmol) were heated to 65° C. in THF for 4 hours. The mixture was allowed to cool, diluted with ethyl acetate (20 mL), and acidified with dilute hydrochloric acid (15 mL). The organic layer was separated off, and the aqueous layer was further extracted with ethyl acetate (2×15 mL). The combined organic fractions were washed with brine, dried ($MgSO_4$), and the solvent was evaporated under reduced pressure. The residue was chromatographed ($SiO_2$, heptane/ethyl acetate, 98:2) to give a 9:1 ratio of nitro-esters 5 and 6 (0.35 g, 60%) as a yellow oil; Rf (heptane/ethyl acetate, 9:1) 0.28; $v_{max}$(film)/cm$^{-1}$ 1732 (C=O), 1547 ($NO_2$), 1375 ($NO_2$); major isomer 5: $\delta_H$ (400 MHz; $CDCl_3$): 4.61 (2H, s, $CH_2NO_2$), 4.15 (2H, q, J=7.2, $OCH_2Me$), 2.70 (2H, s, $CH_2CO_2Et$), 2.06 (2H, m), 1.81 (2H, dd, J=13.9, 7.1), 1.56 (2H, dd, J=13.1, 6.8), 1.51–1.22 (8H, m) 1.28 (3H, t, J=7.2).

Synthesis of Compounds 7 and 8

The mixture of 5 and 6 (0.81 g, 3.01 mmol) in methanol (30 mL) was shaken over a catalytic amount of nickel sponge catalyst under a hydrogen atmosphere (50 Psi, 30° C.) for 12 hours. The mixture was filtered, and the solvent was evaporated under reduced pressure to give a 9:1 mixture of amino-esters 7 and 8 (0.42 g, 72%) as a white solid; $v_{max}$(film)/cm$^{-1}$ 3214 (NH), 1706 (C=O); major isomer 7: $\delta_H$ (400 MHz; $CDCl_3$): 5.57 (1H, br s, NH), 3.20 (2H, s, $CH_2NH$), 2.36 (2H, s, $CH_2CO$), 2.04–1.94 (2H, m), 1.77 (2H, dd, J=13.2, 7.0), 1.62 (2H, dd, J=13.4, 6.7), 1.60–1.20 (8H, m); m/z (ES+) 387 (2M+H, 97%).

Synthesis of Compounds 9 and 10 and Resolution of Compound 9

(1α,6α,8α)(2-Aminomethyl-octahydro-inden-2-yl)-acetic acid hydrochloride

The mixture of 7 and 8 (0.42 g, 2.17 mmol) was dissolved in 1,4-dioxane (8 mL) and hydrochloric acid (20 mL of a 6N solution), and the mixture was refluxed for 6 hours. After cooling, the mixture was diluted with water (20 mL) and washed with dichloromethane (2×15 mL). The aqueous layer was evaporated under reduced pressure to give a 9:1 mixture of acids 9 and 10 (0.43 g, 79%) as a white solid. Recrystallization using ethyl acetate/methanol gave acid 9 exclusively (0.27 g); $\delta_H$(400 MHz; $d_6$-DMSO): 12.3 (1H, br s, $CO_2H$), 7.94 (2H, br s, $NH_2$), 2.90 (2H, s, $CH_2NH_2$), 2.52 (2H, s, $CH_2CO_2H$), 1.97 (2H, br s), 1.65 (2H, dd, J=13.5, 6.7), 1.54–1.20 (10H, m); m/z (ES+) 212 (M+H, 100%); (Found: C, 56.4; H, 8.74; N, 5.43 $C_{12}H_{21}NO_2 \cdot 1HCl0.5H_2O$ requires C, 56.1; H, 9.03; N, 5.45%); LCMS (Prodigy C18 50 mm×4.6 mmid column, 5%–50% Acetonitrile/water); Retention Time=1.53 minutes, 98% purity.

Example 5

((1α,6α,8 β)(2-Aminomethyl-octahydro-inden-2-yl)-acetic acid hydrochloride

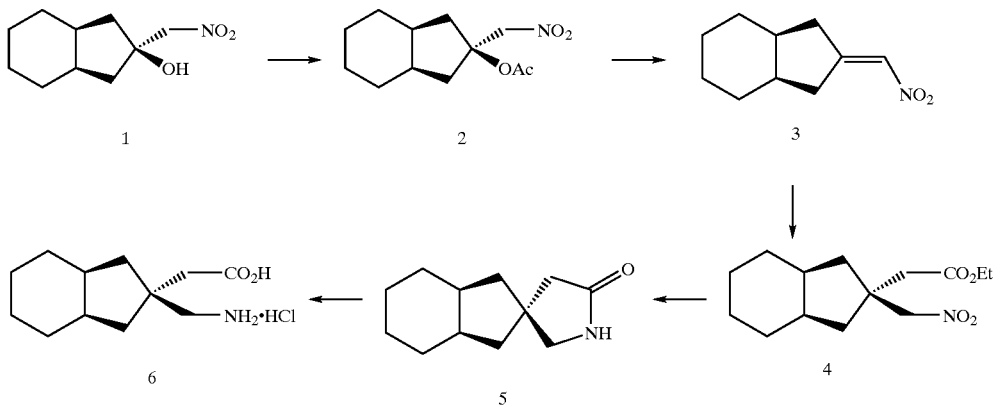

Synthesis of Compound 1 n-Butyllithium (5.1 mL of a 2.5 M solution in hexanes, 12.75 mmol) was added dropwise to a stirring mixture of nitromethane (0.34 mL, 6.3 mmol) in THF (20 mL) and HMPA (2 mL) at −78° C. under argon. The mixture was allowed to warm to −60° C. and stirred for 1 hour. The mixture was cooled to −78° C. and 3 (0.79 g, 5.73 mmol) was added. The mixture was allowed to warm to −60° C. and stirred for a further 2 hours. The mixture was quenched by addition of saturated ammonium chloride solution (5 mL). After warming to room temperature, dilute hydrochloric acid (10 mL) and ether (30 mL) were added. The organic layer was separated, and the aqueous layer was further extracted with ether (2×25 mL). The combined organic fractions were washed with brine, dried ($MgSO_4$), and the solvent was evaporated under reduced pressure. The residue was chromatographed ($SiO_2$, heptane/ethyl acetate, 95:5) to give the nitro-alcohol 1 (0.50 g, 43%) as a white solid; Rf (heptane/ethyl acetate, 9:1) 0.14; $v_{max}$($CH_2Cl_2$)/cm$^{-1}$ 3424 (OH), 1548 ($NO_2$), 1379 ($NO_2$); $\delta_H$(400 MHz; $CDCl_3$): 4.45 (2H, s, $CH_2NO_2$), 3.26 (1H, s, OH), 2.04–1.95 (2H, m), 1.85–1.80 (4H, m), 1.64–1.24 (8H, m).

Synthesis of Compound 2

A mixture of 1 (0.50 g, 2.49 mmol) and concentrated sulphuric acid (1 drop) was heated to 50° C. in acetic anhydride (1 mL) for 5 minutes. The mixture was allowed to cool and then partitioned between ether (100 mL) and water (50 mL). The ether layer was washed with brine, dried ($MgSO_4$), and the solvent was evaporated under reduced pressure to give the nitro-acetate 2 (0.49 g, 82%) as a colorless oil; Rf (heptane/ethyl acetate, 9:1) 0.44; vmax (film)/cm$^{-1}$ 1739 (C=O), 1551 ($NO_2$), 1375 ($NO_2$); δH (400 MHz; $CDCl_3$): 4.88 (2H, s, $CH_2NO_2$), 2.38–2.00 (8H, m), 2.07 (3H, s, MeCO), 1.62–1.32 (6H, m).

Synthesis of Compound 3

Potassium methoxide (0.15 g, 2.04 mmol) in methanol (3 mL) was added dropwise to a stirring solution of 2 (0.49 g, 2.04 mmol) in methanol (5 mL) at 0° C. After 10 minutes, the mixture was partitioned between ether (100 mL) and water (50 mL). The ether layer was washed with brine, dried (MgSO$_4$) and the solvent was evaporated under reduced pressure. The residue was chromatographed (SiO$_2$, pentane/ether, 98:2) to give the nitro-alkene 3 (0.21 g, 57%) as a pale yellow oil; R$_f$ (heptane/ethyl acetate, 8:2) 0.54; vmax(film)/cm$^{-1}$ 1643 (C=C), 1509 (NO$_2$), 1342 (NO$_2$); $\delta_H$(400 MHz; CDCl$_3$): 7.12 (1H, quin, J=2.0, CHNO$_2$), 3.01 (1H, ddt, J=20.5, 8.0, 2.1), 2.90 (1H, ddt, J=20.5, 7.3, 2.1), 2.54 (1H, ddt, J=17.8, 7.1, 2.0), 2.43 (1H, ddt, J 17.7, 5.6, 1.9), 2.21 (1H, m), 2.12 (1H, m), 1.60–1.24 (8H, m).

Synthesis of Compound 4

Ethyl acetate (0.12 mL, 1.22 mmol) in THF (2 mL) was added dropwise to a stirring solution of lithium bis(trimethylsilyl)amide (1.22 mL of a 1 M solution in THF, 1.22 mmol) at −78° C. under argon. After 20 minutes, 3 (0.21 g, 1.16 mmol) in THF (1 mL) was added, and the mixture was stirred for 2 hours. The mixture was quenched by addition of saturated ammonium chloride solution (3 mL) and allowed to warm to room temperature. The mixture was diluted with ether (20 mL) and dilute hydrochloric acid (15 mL) was added. The organic layer was separated, and the aqueous layer was further extracted with ether (2×10 mL). The combined organic fractions were washed with brine, dried (MgSO$_4$), and the solvent was evaporated under reduced pressure. The residue was chromatographed (SiO$_2$, heptane/ethyl acetate, 99:1) to give the nitro-ester 4 (0.13 g, 41%) as a colorless liquid; Rf (heptane/ethyl acetate, 9:1) 0.32; v$_{max}$(film)/cm$^{-1}$ 1731 (C=O), 1547 (NO$_2$), 1375 (NO$_2$); $\delta$H (400 MHz; CDCl$_3$): 4.73 (2H, s, CH$_2$NO$_2$), 4.14 (2H, q, J=7.1, CO$_2$CH$_2$Me), 2.58 (2H, s, CH$_2$CO$_2$Et), 2.07 (2H, m), 1.71–1.66 (4H, m), 1.60–1.24 (8H, m), 1.26 (3H, t, J=7.2, CO$_2$CH$_2$Me); m/z (ES$^+$) 270 (M+H, 100%).

Synthesis of Compound 5

4 (0.122 g, 0.45 mmol) in methanol (40 mL) was shaken over a catalytic amount of nickel sponge catalyst under a hydrogen atmosphere (60 Psi, 30° C.) for 6 hours. The mixture was filtered and the solvent was evaporated under reduced pressure to give amino-ester 5 (0.084 g, 96%) as a white solid; v$_{max}$(film)/cm$^{-1}$ 3228 (NH), 1665 (C=O); $\delta_H$ (400 MHz; CDCl$_3$): 5.49 (1H, br s, NH), 3.34 (2H, s, CH$_2$NH), 2.25 (2H, s, CH$_2$CO), 2.10–1.98 (2H, m), 1.77 (2H, dd, J=13.2, 7.1), 1.65 (2H, dd, J=13.2, 6.8), 1.62–1.20 (8H, m).

Synthesis of Compound 6

(2-Aminomethyl-octahydro-inden-2-yl)-acetic acid 5 (0.083 g, 0.43 mmol) was dissolved in 1,4-dioxane (2 mL) and hydrochloric acid (8 mL of a 6N solution), and the mixture was refluxed for 5 hours. After cooling, the mixture was diluted with water (20 mL) and washed with dichloromethane (2×15 mL). The aqueous layer was evaporated under reduced pressure to give the acid 6 (0.097 g, 91%) as a white solid. This was recrystallized using ethyl acetate/methanol to give pure 10 (0.057 g); 6H (400 MHz; d$_6$-DMSO): 7.90 (2H, br s, NH$_2$), 3.02 (2H, s, CH$_2$NH$_2$), 2.43 (2H, s, CH$_2$CO$_2$H), 2.00 (2H, br s), 1.53–1.24 (12H, m); m/z (ES+)212(M+H, 100%); LCMS (Prodigy C18 50 mm×4.6 mmid column, 5%–50% Acetonitrile/water) Retention Time=1.12 minutes, 100% purity.

Example 6

(1α,3α,5α)-3-aminomethyl-bicyclo[3.2.0]heptane-3-acetic acid

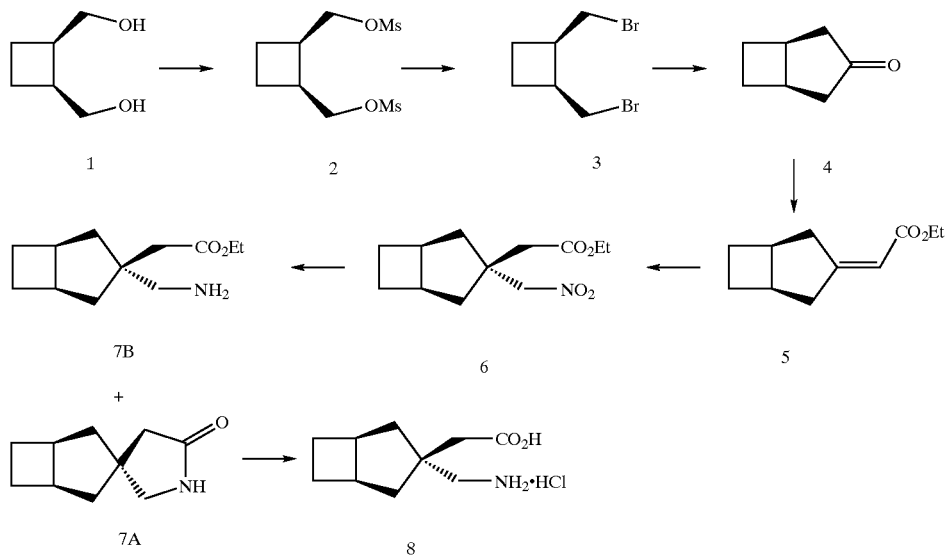

Synthesis of Compound 1

Lithium aluminum hydride (69.4 mL of a 1 M solution in ether, 69.4 mmol) was added dropwise to a stirring solution of cis-cyclobutane-1,2-dicarboxylic acid (5 g, 34.7 mmol) in THF (60 mL) at 0° C. under argon. The mixture was allowed to warm to room temperature and stirred for 16 hours. The mixture was cooled to 0° C. and quenched by careful addition of water (2.7 mL), sodium hydroxide solution (2.7 mL of a 15% w/v solution), and water (8.1 mL). The mixture was stirred for 15 minutes, and the precipitate was removed by filtration. The solvent was evaporated under reduced pressure to give the alcohol 1 as a colorless oil (4.0 g, 98%); 8H (400 MHz; CDCl$_3$): 3.85 (2H, m), 3.6 (2H, m), 3.2 (2H, s), 2.7 (2H, m), 2 (2H, m), 1.55 (2H, m); $^6$C (400 MHz; CDCl$_3$): 63.15, 37.83, 20.40.

Synthesis of Compound 2

Mesyl chloride (6.2 mL, 79.1 mmol) was added dropwise to a stirring solution of 1 (4.0 g, 34.4 mmol) in dichloromethane (150 mL) at −40° C. under argon. Triethylamine (12.0 mL, 86.0 mmol) was then added dropwise, and the mixture was allowed to warm slowly to room temperature. After stirring for 16 hours, the mixture was quenched by addition of dilute hydrochloric acid (50 mL). The organic layer was separated, and the aqueous layer was further extracted with dichloromethane (2×50 mL). The combined organic fractions were washed with brine, dried (MgSO$_4$), and the solvent was evaporated under reduced pressure. The residue was chromatographed (SiO$_2$, heptane/ethyl acetate, 6:4) to give the mesylate 2 (6.1 g, 73%) as a white solid; Rf (heptane/ethyl acetate, 1:1) 0.18. $\delta_H$(400 MHz; CDCl$_3$): 4.3 (4H, m), 3.05 (6H, s), 2.9 (2H, m), 2.2 (2H, m), 1.8 (2H, m); $\delta_c$(400 MHz; CDCl$_3$): 69.51, 37.45, 35.28, 21.09.

Synthesis of Compound 3

Anhydrous lithium bromide (10.6 g, 121.8 mmol) was added to a stirring mixture of 2 (5.95 g, 24.4 mmol) in acetone (50 mL) under argon and the mixture was refluxed for 2 hours. After cooling, the acetone was evaporated under reduced pressure and the residue was taken up in ether (50 mL), washed with water (50 mL), brine, dried (MgSO$_4$), and the solvent was evaporated under reduced pressure. The residue was chromatographed (SiO$_2$, heptane/ethyl acetate, 95:5) to give the dibromide 3 (5.36 g, 86%) as an orange liquid; Rf (heptane-ethyl acetate, 8:2), 0.82. $\delta_H$(400 MHz; CDCl$_3$): 3.6 (2H, m), 3.45 (2H, m), 2.85 (2H, m), 2.1 (2H, m), 1.7 (2H, m; $\delta_c$(400 MHz; CDCl$_3$): 39.70, 33.79, 23.95.

Synthesis of Compound 4

To a cooled (0° C.) suspension of potassium hydride (1.58 g, 39.5 mmol) (previously washed 3 times with pentane) in tetrahydrofuran (22 mL) was added, under an argon atmosphere, a solution of methyl methylthiomethyl sulfoxide (1.36 mL, 13.04 mmol, previously dried over molecular sieves for 3 hours) in tetrahydrofuran (3 mL) over 1 hour. After stirring for a further 30 minutes, a solution of 3 (3.17 g, 13.1 mmol) in THF (2 mL) was added, at 0° C., over 1 hour. The reaction mixture was then allowed to warm up to room temperature and was stirred overnight. The mixture was quenched by addition of aqueous ammonium chloride (6 mL, 25%). After 10 minutes, the solid was filtered off and the filtrate concentrated. The residue was taken up in ether (20 mL) and 9N sulfuric acid (0.05 mL) was added. After stirring for 30 hours, saturated sodium hydrogen carbonate was added. The ether phase was separated and concentrated to 5 mL. Saturated sodium hydrogen sulphite (1.5 g) solution was added and the mixture stirred for 30 minutes. The phases were separated. The ethereal phase was stirred for further 30 minutes with a saturated sodium hydrogen sulphite (0.5 g) solution. The phases were separated and the collected aqueous phases were treated with aqueous sodium hydroxide (5 mL, 20%) and extracted with ether. The ether phase was dried (MgSO$_4$) and evaporated under reduced pressure to give 4 as a yellow liquid (0.16 g, 11%). $\delta_H$(400 MHz; CDCl$_3$): 3.0 (2H, m), 2.15–2.45 (6H, m), 1.65 (2H, m).

Synthesis of Compound 5

Triethyl phosphonoacetate (0.32 mL, 1.61 mmol) was added dropwise to a stirring suspension of sodium hydride (0.059 g of a 60% dispersion in oil, 1.47 mmol) in THF (2 mL) at 0° C. under argon. After 20 minutes, ketone 4 (0.16 g, 1.45 mmol) in THF (1 mL) was added dropwise. The mixture was allowed to warm to room temperature and stirred for 16 hours. Water (5 mL) was added and the mixture was extracted with ethyl acetate. The combined organic fractions were washed with brine and dried (MgSO$_4$). The solvent was evaporated under reduced pressure. The residue was chromatographed (SiO$_2$, heptane/ethyl acetate, 95:5) to give the ester 5 (0.166 g, 0.92 mmol, 64%) as a colorless oil; $\delta_H$(400 MHz; CDCl$_3$): 5.9 (1H, s), 4.2 (2H, q), 3.15 (1H, d), 2.9 (1H, m), 2.8 (1H, m); 2.65 (2H, m), 2.3 (1H, d), 2.15 (2H, m), 1.5 (2H, m), 1.3 (3H, t); $\delta_C$(400 MHz; CDCl$_3$): 169.51, 166.98, 113.37, 59.62, 43.23, 38.79, 38.45, 36.20, 25.62, 24.95, 14.44.

Synthesis of Compound 6

Ester 5 (0.152 g, 0.84 mmol), nitromethane (0.092 mL, 1.7 mmol), and tetra-butylammonium fluoride (1.03 mL of a 1 M solution in THF, 1.03 mmol) were heated to 65° C. in THF (1 mL) for 4 hours. The mixture was allowed to cool, diluted with ether (30 mL), and acidified with 2N hydrochloric acid (5 mL). The organic layer was washed with brine, dried (MgSO$_4$), and the solvent was evaporated under reduced pressure. The residue was chromatographed (SiO$_2$, heptane/ether, 95:5) to give nitro-ester 6 (0.085 g, 0.35 mmol, 41%) as a colorless liquid; $\delta_H$(400 MHz; CDCl$_3$): 4.4 (2H, s), 4.15 (2H, q), 2.75 (2H, bs), 2.7 (2H, s), 2.3 (2H, m); 2.1 (2H, m), 1.65 (4H, m), 1.15 (3H, t); $\delta_C$(400 MHz; CDCl$_3$): 171.48, 79.68, 60.52, 50.10, 44.15, 41.06, 37.36, 25.76, 14.28.

Synthesis of Compounds 7A and 7B

Nitro-ester 6 (0.076 g, 0.31 mmol) in methanol (10 mL) was shaken over a catalytic amount of nickel sponge catalyst under a hydrogen atmosphere (50 Psi, 30° C.) for 12 hours. The mixture was filtered, and the solvent was evaporated under reduced pressure to give a mixture of lactam 7A and amino-ester 7B (0.05 g) as a white solid. This was used without further purification and characterization.

Synthesis of Compound 8

7A and 7B (0.05 g) were dissolved in hydrochloric acid (2 mL of a 6N solution), and the mixture was refluxed for 4 hours. After cooling, solvent was evaporated under reduced pressure to give the acid as a white solid. This was recrystallized using ethyl acetate/methanol to give pure 8 (0.045 g, 0.2 mmol, 64%); $\delta_H$(400 MHz; D$_2$O): 3 (2H, s), 2.85 (4H, M+s), 2.35 (2H, m), 2.1 (2H, m), 1.75 (4H, m). $\delta_C$(400 MHz; D$_2$O): 167.5, 46.64, 43.89, 42.03, 40.89, 36.08, 23.91. m/z (ES$^+$) 184 (M+H, 100%).

Example 7

(±)-(1α, 5β) (3-aminomethyl-bicyclo[3.2.0]hepty-3-yl)-ascetic acid hydrochloride

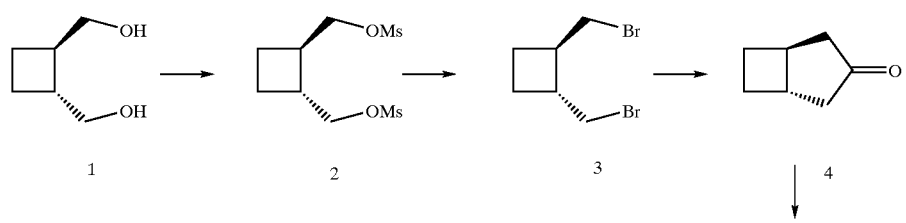

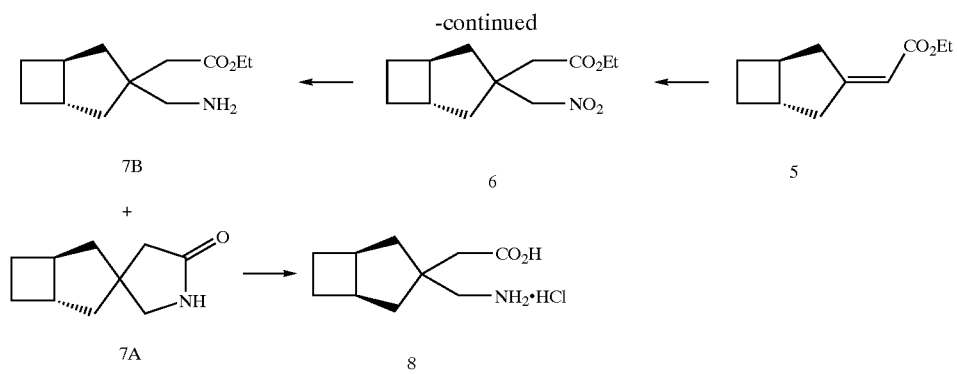

Synthesis of Compound 1

Lithium aluminum hydride (134.8 mL of a 1 M solution in ether, 134.8 mmol) was added dropwise to a stirring solution of cis-cyclobutane-1,2-dicarboxylic acid (9.71 g, 67.39 mmol) in THF (120 mL) at 0° C. under argon. The mixture was allowed to warm to room temperature and stirred for 16 hours. The mixture was cooled to 0° C. and quenched by careful addition of water (5.2 mL), sodium hydroxide solution (5.2 mL of a 15% w/v solution), and water (15.7 mL). The mixture was stirred for 15 minutes, and the precipitate was removed by filtration. The solvent was evaporated under reduced pressure to give the alcohol 1 as a pale yellow oil (6.73 g, 57.64 mmol, 85%); $\delta_H$ (400 MHz; $CDCl_3$): 3.85 (2H, m), 3.6 (2H, m), 2.9 (2H, s), 2.7 (2H, m), 2 (2H, m); 1.55 (2H, m).

Synthesis of Compound 2

Mesyl chloride (29.3 mL, 373.8 mmol) was added dropwise to a stirring solution of 1 (8.85 g, 75.8 mmol) in dichloromethane (500 mL) at −40° C. under argon. Triethylamine (63.4 mL, 454.4 mmol) was then added dropwise, and the mixture was allowed to warm slowly to room temperature. After stirring for 16 hours, the mixture was quenched by addition of dilute hydrochloric acid (100 mL). The organic layer was separated, and the aqueous layer was further extracted with dichloromethane (2×100 mL). The combined organic fractions were washed with brine, dried ($MgSO_4$), and the solvent was evaporated under reduced pressure. The residue was chromatographed ($SiO_2$, heptane/ethyl acetate, 6:4) to give the mesylate 2 (15.89 g, 58.3 mmol, 77%) as a white solid; $\delta_H$ (400 MHz; $CDCl_3$): 3.0 (6H, m), 2.6 (2H, m), 2.05 (2H, m), 1.8 (2H, m).

Synthesis of Compound 3

Anhydrous lithium bromide (25 g, 287.3 mmol) was added to a stirring mixture of 2 (15.84 g, 57.4 mmol) in acetone (150 mL) under argon, and the mixture was refluxed for 2 hours. After cooling, the acetone was evaporated under reduced pressure, and the residue was taken up in ether (100 mL), washed with water (100 mL), brine, dried ($MgSO_4$), and the solvent was evaporated under reduced pressure to give the dibromide 3 (13.5 g, 55.8 mmol, 97%) as an orange liquid; $\delta_H$ (400 MHz; $CDCl_3$): 3.5 (4H, m), 2.45 (2H, m), 2.05 (2H, m), 1.6 (2H, m).

Synthesis of Compound 4

To a cooled (0° C.) suspension of potassium hydride (1.08 g, 27 mmol) (previously washed 3 times with pentane) in THF (15 mL) was added, under an argon atmosphere, a solution of methyl methylthiomethyl sulfoxide (0.93 mL, 8.92 mmol, previously dried over molecular sieves for 3 hours) in THF (2 mL) over a period of 1 hour. After stirring for a further 30 minutes, a solution of 3 (2.16 g, 8.93 mmol) in THF (1 mL) was added, at 0° C., over a period of 1 hour. The reaction mixture was then allowed to warm up to room temperature and was stirred overnight. The mixture was quenched by addition of aqueous ammonium chloride (6 mL, 25%). After 10 minutes, the solid was filtered off and the filtrate concentrated. The residue was taken up in ether (20 mL), and 9N sulfuric acid (0.03 mL) was added. After stirring for 30 hours, saturated sodium hydrogen carbonate was added. The ether phase was separated and concentrated to 5 mL. Saturated sodium hydrogen sulphite (1.5 g) solution was added and the mixture stirred for 30 minutes. The phases were separated. The ethereal phase was stirred for further 30 minutes with a saturated sodium hydrogen sulphite (0.5 g) solution. The phases were separated and the collected aqueous phases were treated with aqueous sodium hydroxide (5 mL, 20%) and extracted with ether. The ether phase was dried ($MgSO_4$) and the solvent was evaporated under reduced pressure to give 4 as a yellow liquid (0.141 g, 15%); $\delta_H$ (400 MHz; $CDCl_3$): 2.25 (4H, m), 2.0 (4H, m), 1.7 (2H, m).

Synthesis of Compound 5

Triethyl phosphonoacetate (0.28 mL, 1.41 mmol) was added dropwise to a stirring suspension of sodium hydride (0.052 g of a 60% dispersion in oil, 1.29 mmol) in THF (2 mL) at 0° C. under argon. After 20 minutes, ketone 4 (0.141 g, 1.28 mmol) in THF (1 mL) was added dropwise. The mixture was allowed to warm to room temperature and stirred for 16 hours. Water (5 mL) was added, and the mixture was extracted. The combined organic fractions were washed with brine and dried ($MgSO_4$). The solvent was evaporated under reduced pressure. The residue was chromatographed ($SiO_2$, heptane/ethyl acetate, 95:5) to give the ester 5 (0.092 g, 0.51 mmol, 40%) as a colorless oil; $\delta_H$ (400 MHz; $CDCl_3$): 5.85 (1H, s), 4.1 (2H, q), 3.1 (1H, d.d), 2.45 (1H, d.d), 2.2 (2H, m), 1.75 (2H, m), 1.4 (2H, m), 1.25 (3H, t); $\delta_C$ (400 MHz; $CDCl_3$): 170.53, 166.57, 115.13, 59.62, 47.06, 45.69, 39.89, 37.24, 28.52, 28.17, 14.44.

Synthesis of Compound 6

Ester 5 (0.09 g, 0.5 mmol), nitromethane (0.055 mL, 1.02 mmol), and tetra-butylammonium fluoride (0.61 mL of a 1 M solution in TBF, 0.61 mmol) were heated to 65° C. in THF (1 mL) for 4 hours. The mixture was allowed to cool, diluted with ether (30 mL), and acidified with 2N hydrochloric acid (5 mL). The organic layer was washed with brine, dried ($MgSO_4$), and the solvent was evaporated under reduced pressure. The residue was chromatographed ($SiO_2$, heptane/ether, 95:5) to give nitro-ester 6 (0.063 g, 0.26 mmol, 52%) as a colorless liquid. $\delta_H$ (400 MHz; $CDCl_3$): 4.65 (2H, [AB]q), 4.15 (2H, q), 2.65 (2H, [AB]q), 1.2–1.95 (3H, t and m, 13H); $\delta_C$ (400 MHz; $CDCl_3$): 171.28, 82.42, 60.56, 49.97, 45.80, 45.32, 42.88, 40.19, 40.09, 27.64, 14.26.

Synthesis of Compounds 7A and 7B

Nitro-ester 6 (0.063 g, 0.26 mmol) in methanol (10 mL) was shaken over a catalytic amount of nickel sponge catalyst under a hydrogen atmosphere (50 Psi, 30° C.) for 12 hours. The mixture was filtered, and the solvent was evaporated under reduced pressure to give a mixture of lactam 7A and amino-ester 7B (0.051 g) as a white solid. This was used without further purification and characterization.

Synthesis of Compound 8

7A and 7B (0.051 g) were dissolved in hydrochloric acid (2 mL of a 6N solution) and the mixture was refluxed for 4 hours. After cooling, solvent was evaporated under reduced pressure to give the acid as a white solid. This was recrystallized using ethyl acetate/methanol to give pure 8 (0.046 g, 0.21 mmol, 81%); $\delta_H$ (400 MHz; D$_2$O): 3.3 (2H, [AB]q), 2.7 (2H, [AB]q), 2 (2H, m), 1.35–1.85 (8H, m); $^8$C (400 MHz; D$_2$O): 174.8, 47.50, 46.59, 44.28, 43.61, 41.64, 38.37, 38.09, 25.88. m/z (ES$^+$) 184 (M+H, 100%).

Example 8
(1α,3β,5α)(3-Aminomethyl-bicyclo[3.2.0]hept-3-yl)-acetic acid hydrochloride

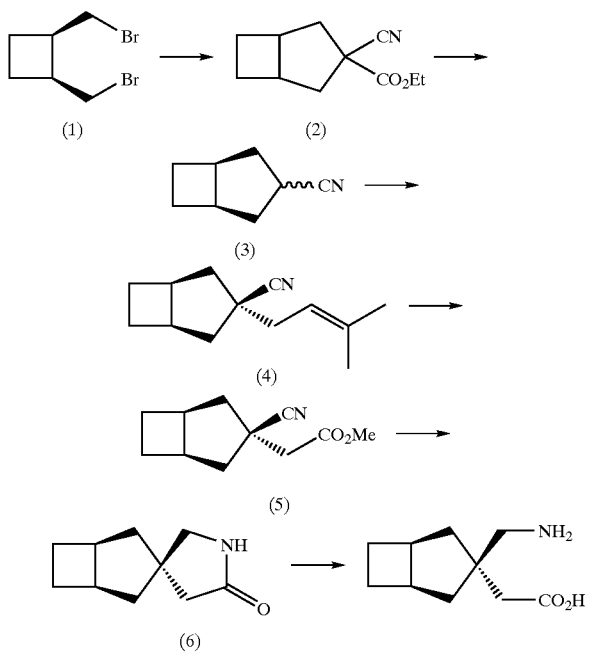

Synthesis of Compound 2

Dibromide 1 (5.7 g, 22.3 mmol), ethyl cyanoacetate (4.8 mL, 44.5 mmol) and potassium carbonate (6.15 g, 44.5 mmol) were stirred together in DMF (100 mL) for 48 hours. Dilute hydrochloric acid (100 mL) was added, and the mixture was extracted with ether (3×100 mL). The combined organic fractions were washed with brine, dried (MgSO$_4$), and the solvent was evaporated under reduced pressure. The residue was chromatographed (SiO$_2$, heptane-ethyl acetate, 98:2) to give the cyanoester 2 (4.3 g, 100%) as a 68:32 mixture of diastereoisomers; R$_f$(heptane-ethyl acetate, 9:1) 0.28; $v_{max}$(film)/cm$^{-1}$ 2241 (CN), 1741 (C=O); Major diastereoisomer: $\delta_H$(400 MHz; CDCl$_3$) 4.30 (2H, q, J 7.1, CO$_2$CH$_2$Me), 2.98 (2H, m), 2.56–2.22 (6H, m), 1.70 (2H, m), 1.35 (3H, t, J 7.1, Me); Minor diastereoisomer: $\delta_H$ (400 MHz; CDCl$_3$) 4.26 (2H, q, J 7.1, CO$_2$CH$_2$Me), 3.05 (2H, m), 2.56–2.22 (6H, m), 1.99 (2H, m), 1.33 (3H, t, J 7.1, Me).

Synthesis of Compound (3)

Cyanoester 2 (0.76 g, 3.91 mmol), water (0.14 mL, 7.82 mmol) and lithium chloride (0.66 g, 15.6 mmol) were heated to 150° C. in DMSO (40 mL) for 22 hours. The mixture was allowed to cool, diluted with water (150 mL) and extracted with ether (3×50 mL). The combined ether fractions were washed with brine, dried (MgSO$_4$), and the solvent was evaporated under reduced pressure. The residue was chromatographed (SiO$_2$, heptane-ethyl acetate, 95:5) to give the cyanide 3 (0.21 g, 44%) as a 60:40 mixture of diastereoisomers; R$_f$(heptane-ethyl acetate, 9:1) 0.44; $v_{max}$(film)/cm$^{-1}$ 2238 (CN); Major diastereoisomer: $\delta_H$ (400 MHz; CDCl$_3$) 2.97 (1H, m), 2.87 (2H, m), 2.32–2.18 (2H, m), 2.10–1.96 (3H, m), 1.92–1.78 (2H, m), 1.48–1.38 (1H, m); Minor diastereoisomer: $\delta_H$ (400 MHz; CDCl$_3$) 3.13 (1H, m), 2.87 (2H, m), 2.32–2.18 (2H, m), 2.10–1.96 (3H, m), 1.92–1.78 (2H, m), 1.48–1.38 (1H, m).

Synthesis of Compound (4)

Cyanide 3 (0.86 g, 7.1 mmol) in THF (30 mL) was added dropwise over 1 hour to a stirring mixture of lithium hexamethyldisilazide (7.8 mL of a 1 M solution in THF, 7.8 mmol) in THF (40 mL) at −78° C. under argon. The mixture was allowed to warm to −40° C. and stirred for 2 hours. The mixture was cooled to −78° C. and dimethylallyl bromide (1.3 mL, 10.6 mmol) was added. The mixture was stirred for a further 2 hours at −78° C. and then allowed to warm to room temperature overnight. Saturated ammonium chloride solution (20 mL) was added, and the mixture was diluted with ether (50 mL) and dilute hydrochloric acid (30 mL). The aqueous layer was further extracted with ether (2×50 mL), and the combined organic fractions were washed with brine, dried (MgSO$_4$), and the solvent was evaporated under reduced pressure. The residue was chromatographed (SiO$_2$, heptane-ethyl acetate, 98:2) to give the cyanoalkene 4 (0.96 g, 72%) as a colorless oil; R$_f$(heptane-ethyl acetate, 95:5) 0.38; $v_{max}$(film)/cm$^{-1}$ 2230 (CN), 1673 (C=C); $\delta_H$ (400 MHz; CDCl$_3$) 5.27 (1H, tt, J 7.6, 1.3, CHCMe$_2$), 2.89 (2H, m), 2.30–2.22 (4H, m), 2.10 (2H, d, J 14.2), 1.94 (2H, m), 1.84–1.62 (2H, m), 1.65 (3H, s, Me), 1.55 (3H, s, Me); m/z (AP$^+$) 190 (M+H, 100%).

Synthesis of Compound (5)

Cyanoalkene 4 (0.96 g, 5.1 mmol) and sodium hydroxide (10.2 mL of a 2.5 M solution in methanol, 25.5 mmol) were stirred together in dichloromethane (80 mL) at −78° C. Ozone was passed through the mixture which immediately went orange. After 2 hours, the mixture turned to a green color, and the solution was purged with oxygen for 5 minutes and then with nitrogen. The stirring mixture was diluted with ether (100 mL) and water (100 mL) and allowed to warm to room temperature overnight. The aqueous layer was further extracted with ether (2×50 mL), and the combined organic fractions were washed with brine, dried (MgSO$_4$), and the solvent was evaporated under reduced pressure. The residue was chromatographed (SiO$_2$, heptane-ethyl acetate, 95:5) to give the cyanoester 5 (0.70 g, 71%) as a yellow oil; R$_f$(heptane-ethyl acetate, 8:2) 0.36; $v_{max}$(film)/cm$^{-1}$ 2233 (CN), 1740 (C=O); $\delta_H$ (400 MHz; CDCl$_3$) 3.75 (3H, s, OMe), 2.94 (2H, m), 2.63 (2H, s, CH$_2$CO$_2$Me), 2.35–2.21 (4H, m), 2.00 (2H, m), 1.86 (2H, m); m/z (AP$^+$) 194 (M+H, 95%).

Synthesis of Compound (6)

Cyanoester 5 (0.81 g, 4.2 mmol) in methanol (100 mL) was shaken over a catalytic amount of nickel sponge catalyst under a hydrogen atmosphere (60 Psi, 30° C.) for 6 hours. The mixture was filtered, and the solvent was evaporated under reduced pressure to give lactam 6 (0.64 g, 92%) as a white solid; $v_{max}$(film)/cm$^{-1}$ 1692 (C=O); 5H (400 MHz; CDCl$_3$ 5.52 (1H, br s, NH), 3.54 (2H, s, CH$_2$NH), 2.80 (2H, m), 2.26 (2H, m), 2.16 (2H, s, CH$_2$CO), 1.93 (2H, ddd, J 13.4, 8.1, 2.4), 1.74 (2H, dd, J 13.0, 3.2), 1.64 (2H, m).

Synthesis of (1α,3β,5α)(3-Aminomethyl-bicyclo[3.2.0]hept-3-yl)-acetic acid hydrochloride Lactam 6 (0.64 g, 3.87 mmol) was dissolved in 1,4-dioxane (4 mL) and hydrochloric acid (16 mL of a 6N solution), and the mixture was refluxed for 6 hours. After cooling, the mixture was diluted with water (20 mL) and washed with dichloromethane (2×15 mL). The aqueous layer was evaporated under reduced pressure to give acid 7 (0.67 g, 79%) as a white solid. Recrystallization using ethyl acetate/methanol gave acid 7 exclusively (0.26 g); $\delta_H$ (400 MHz; $d_6$-DMSO) 7.98 (2H, br s, $NH_2$), 3.13 (2H, s, $CH_2NH_2$), 2.70 (2H, s), 2.17–2.14 (4H, m), 1.85 (2H, dd, J 13.3, 8.0), 1.63 (2H, m), 1.55 (2H, dd, J 12.9, 5.1); m/z (ES$^+$) 184 (M+H, 100%); LCMS (Prodigy C18, 50 mm×4.6 mmid column, 5–50% Acetonitrile/water) Retention Time=2.40 minutes, 98% purity.

The following compounds are made by one of the above methods:

(1α,5β)(3-Aminomethyl-bicyclo[3.1.0]hex-3-yl)-acetic acid,
(1α,5β)(3-Aminomethyl-bicyclo[3.2.0]hept-3-yl)-acetic acid,
(1β,5β)(2-Aminomethyl-octahydro-pentalen-2-yl)-acetic acid,
(1α,6β)(2-Aminomethyl-octahydro-inden-2-yl)-acetic acid,
(1α,7β)(2-Aminomethyl-decahydro-azulen-2-yl)-acetic acid,
(1α,5β)(3-Aminomethyl-bicyclo[3.1.0]hex-3-yl)-acetic acid,
(1α,5β)(3-Aminomethyl-bicyclo[3.2.0]hept-3-yl)-acetic acid,
(1α,5β)(2-Aminomethyl-octahydro-pentalen-2-yl)-acetic acid,
(1α,6β)(2-Aminomethyl-octahydro-inden-2-yl)-acetic acid,
(1α,7β)(2-Aminomethyl-decahydro-azulen-2-yl)-acetic acid,
(1α,3α,5α)(3-Aminomethyl-bicyclo[3.1.0]hex-3-yl)-acetic acid,
(1α,3α,5α)-3-aminomethyl-bicyclo[3.2.0]heptane-3-acetic acid,
(1α,3α,5α)(2-Aminomethyl-octahydro-pentalen-2-yl)-acetic acid,
(1α,6α,8α)(2-Aminomethyl-octahydro-inden-2-yl)-acetic acid,
(1α,7α,9α)(2-Aminomethyl-decahydro-azulen-2-yl)-acetic acid,
(1α,3β,5α)(3-Aminomethyl-bicyclo[3.1.0]hex-3-yl)-acetic acid,
(1α,3β,5α)(3-Aminomethyl-bicyclo[3.2.0]hept-3-yl)-acetic acid,
(1α,3β,5α)(2-Aminomethyl-octahydro-pentalen-2-yl)-acetic acid,
(1α,6α,8β)(2-Amninomethyl-octahydro-inden-2-yl)-acetic acid,
(1α,7α,9β)(2-Aminomethyl-decahydro-azulen-2-yl)-acetic acid,
((1R,3R,6R)-3-Aminomethyl-bicyclo[4.1.0]hept-3-yl)-acetic acid,
((1R,3S,6R)-3-Aminomethyl-bicyclo[4.1.0]hept-3-yl)-acetic acid,
((1 S,3S,6S)-3-Aminomethyl-bicyclo[4.1.0]hept-3-yl)-acetic acid,
((1S,3R,6S)-3-Aminomethyl-bicyclo[4.1.0]hept-3-yl)-acetic acid,
((1R,3R,6S)-3-Aminomethyl-bicyclo[4.2.0]oct-3-yl)-acetic acid,
((1R,3S,6S)-3-Aminomethylbicyclo[4.2.0]oct-3-yl)-acetic acid,
((1S,3S,6R)-3-Aminomethyl-bicyclo[4.2.0]oct-3-yl)-acetic acid,
((1S,3R,6R)-3-Aminomethyl-bicyclo[4.2.0]oct-3-yl)-acetic acid,
((3αR,5R,7αS)-5-Aminomethyl-octahydro-inden-5-yl)-acetic acid,
((3αR,5S,7αS)-5-Aminomethyl-octahydro-inden-5-yl)-acetic acid,
((3αS,5S,7αR)-5-Aminomethyl-octahydro-inden-5-yl)-acetic acid,
((3αS,5R,7αR)-5-Aminomethyl-octahydro-inden-5-yl)-acetic acid,
((2R,4αS,7αR)-2-Aminomethyl-decahydro-naphthalen-2-yl)-acetic acid,
((2S,4αS,8αR)-2-Aminomethyl-decahydro-naphthalen-2-yl)-acetic acid,
((2S,4αR,8αS)-2-Aminomethyl-dctahydro-naphthalen-2-yl)-acetic acid,
((2R,4αR,8αS)-2-Aminomethyl-decahydro-naphthalen-2-yl)-acetic acid,
((2R,4αS,9αR)-2-Aminomethyl-decahydro-benzocyclohepten-2-yl)-acetic acid,
((2S,4αS,9αR)-2-Aminomethyl-decahydro-benzocyclohepten-2-yl)-acetic acid,
((2S,4αR,9αS)-2-Aminomethyl-decahydro-benzocyclohepten-2-yl)-acetic acid,
((2R,4αR,9αS)-2-Aminomethyl-decahydro-benzocyclohepten-2-yl)-acetic acid,
((1R, 3R,6S)-3-Aminomethyl-bicyclo[4.1.0]hept-3-yl)-acetic acid,
((1R,4S,6S)-3-Aminomethyl-bicyclo[4.1.0]hept-3-yl)-acetic acid,
((1S,3S,6R)-3-Aminomethyl-bicyclo[4.1.0]hept-3-yl)-acetic acid,
((1S,3R,6R)-3-Aminomethyl-bicyclo[4.1.0]hept-3-yl)-acetic acid,
((1R,3R,6R)-3-Aminomethyl-bicyclo[4.2.0]oct-3-yl)-acetic acid,
((1R,3S,6R)-3-Aminomethyl-bicyclo[4.2.0]oct-3-yl)-acetic acid,
((1S,3S,6S)-3-Aminomethyl-bicyclo[4.2.0]oct-3-yl)-acetic acid,
((1S,3R,6S)-3-Aminomethyl-bicyclo[4.2.0]oct-3-yl)-acetic acid,
((3αR,5R,7αR)-5-Aminomethyl-octahydro-inden-5-yl)-acetic acid,
((3αR,5S,7αR)-5-Aminomethyl-octahydro-inden-5-yl)-acetic acid,
((3αS,5S,7αS)-5-Aminomethyl-octahydro-inden-5-yl)-acetic acid,
((3αS,5R,7αS)-5-Aminomethyl-octahydro-inden-5-yl)-acetic acid,
((2R,4αR,8αR)-2-Aminomethyl-decahydro-naphthalen-2-yl)-acetic acid,
((2S,4αS,8αR)-2-Aminomethyl-decahydro-naphthalen-2-yl)-acetic acid,
((2S,4αR,8αS)-2-Aminomethyl-decahydro-naphthalen-2-yl)-acetic acid,
((2R,4αS,8αS)-2-Aminomethyl-decahydro-naphthalen-2-yl)-acetic acid,
((2R,4αR,9αR)-2-Aminomethyl-decahydro-benzocyclohepten-2-yl)-acetic acid,
((2S,4αR,9αR)-2-Aminomethyl-decahydro-benzocyclohepten-2-yl)-acetic acid,
((2S,4αS,9αS)-2-Aminomethyl-decahydro-benzocyclohepten-2-yl)-acetic acid, and
((2R,4αS,9αS)-2-Aminomethyl-decahydro-benzocyclohepten-2-yl)-acetic acid.

The following methods relate specifically to the preparation of the compound of formula Ia.

Example 9

Method 1

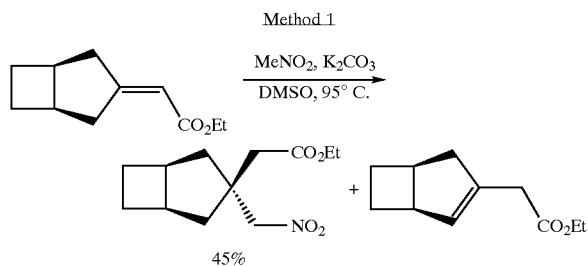

Nitromethane is added to the unsaturated ester in a solvent such as dimethylsulphoxide or N,N-dimethylformamide with a base such as potassium carbonate, sodium carbonate or cesium carbonate, at a temperature of from 0° C. to 120° C. This process achieves higher yields of the nitro ester and reduces the yield of de-conjugated ester compared to previous routes.

removal of water by, for example, use of a Dean-Stark trap or activated molecular sieves, to produce the alkene of formula (2);

b) Adding the product of step a) above to a mixture of benzylmagnesium chloride or benzylmagnesium bromide or benzylmagnesium iodide, in a dry solvent selected from tetrahydrofuran, 1,4-dioxane, n-heptane, toluene, diethyl ether, or tert-butyl methyl ether at a temperature from −100° C. to 110° C. to produce the addition product of formula (3);

c) Adding the product of step b) above to a mixture of a base selected from potassium hydroxide, sodium hydroxide, lithium hydroxide, or cesium hydroxide in a solvent selected from ethylene glycol, 2-methoxyethyl ether, 1,4-dioxane, or diethylene glycol and stirring the mixture at a temperature from 25° C. to 250° C. to produce the carboxylic acid of formula (4);

d) Adding the product of step c) above to a mixture of iodomethane in a solvent selected from dichloromethane, chloroform, tetrahydrofuran, toluene, or 1,4-dioxane to which a base such as 1,8-diazabicyclo[5.4.0]undec-7-ene

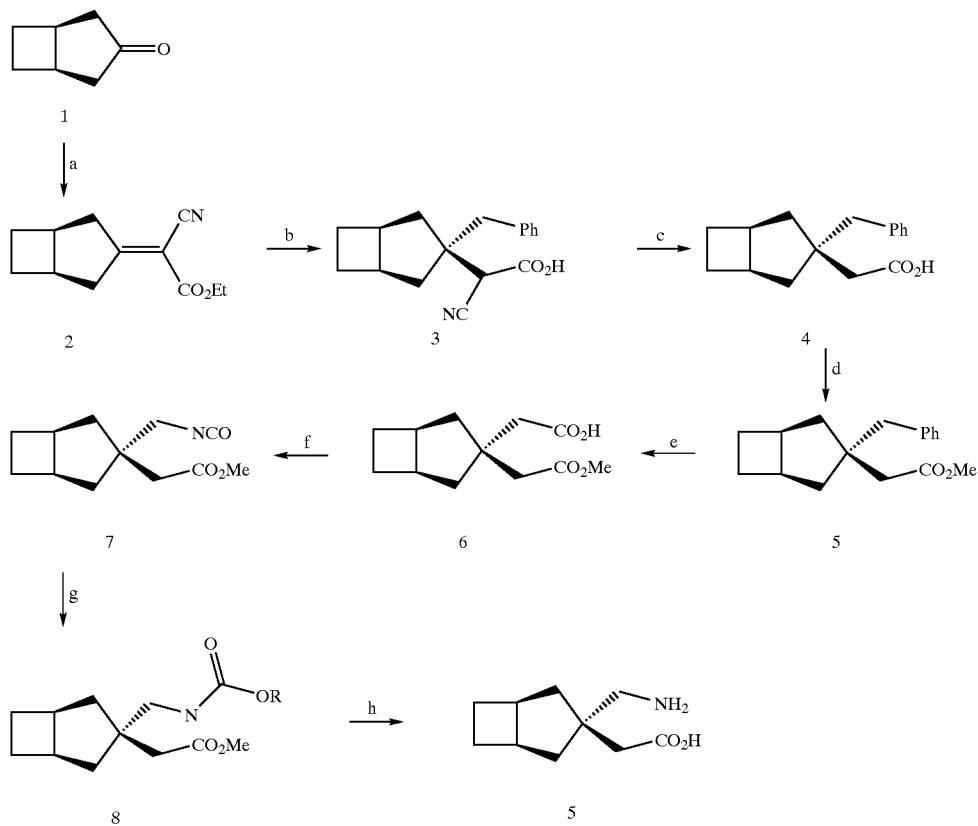

Method 2A a) An alkyl cyanoacetate, for example ethyl cyanoacetate, is added to a mixture of cyclopentanone of formula (1) in a solvent selected from toluene, benzene, xylenes, or n-heptane to which acetic acid and β-alanine or ammonium acetate, or piperidine are added. The mixture is stirred at a temperature from 0° C. to 150° C. with (DBU), triethylamine, or 1,5-diazabicyclo[4.3.0]non-5-ene (DBN) is added and stirred at a temperature from −40° C. to 110° C. to produce the ester of formula (5); or adding the product of step c) above to a mixture of methanol and a concentrated acid such as sulphuric acid or hydrochloric acid at a temperature ranging from 0° C.

to 100° C.; or adding the product of step c) above to trimethylsilyldiazomethane and methanol in benzene or toluene at a temperature from −40° C. to 100° C.; or adding the product of step c) above to diazomethane in a solvent such as benzene, toluene, dichloromethane, or diethyl ether at a temperature from −40° C. to 40° C.;

e) Adding the product of step d) above to a mixture of carbon tetrachloride or ethyl acetate and acetonitrile to which water, sodium periodate, and ruthenium (III) chloride are added, and stirred at a temperature from −40° C. to 80° C. to produce carboxylic acid of formula (6);

f) Adding the product of step e) above to a mixture of a base selected from triethylamine or diisopropylethylamine and a solvent selected from toluene, benzene, xylenes, tetrahydrofuran, diethyl ether, or n-heptane to which diphenylphosphoryl azide (DPPA) is added and stirring at a temperature from 0° C. to 150° C. to produce the isocyanate of formula (7); or adding the product of step e) above to ethyl chloroformate or isobutyl chloroformate and a base such as triethylamine or diisopropylethylamine in tetrahydrofuran or acetone or diethyl ether at a temperature of −40° C. to 78° C. followed by addition of sodium azide in water and tetrahydrofuran or acetone followed by addition of toluene or benzene and refluxing; and g) Adding the product of step f) above to a solvent selected from toluene, benzene, xylenes, or n-heptane to which methanol or tert-butanol was added to give (8) and then adding (8) to aqueous hydrochloric acid at a concentration of from 0.01 M to 12 M in the presence or absence of a solvent such as 1,4-dioxane, acetic acid or water to produce the amino acid (9); or adding the product of step f) above to a solvent selected from toluene, benzene, xylenes, or n-heptane to which benzyl alcohol was added to give (8) and then hydrogenating (8) over nickel or palladium or platinum to give lactam which was then hydrolysed using aqueous hydrochloric acid at a concentration of from 0.01 M to 12 M in the presence or absence of a solvent such as 1,4-dioxane, acetic acid, or water to produce the amino acid (9).

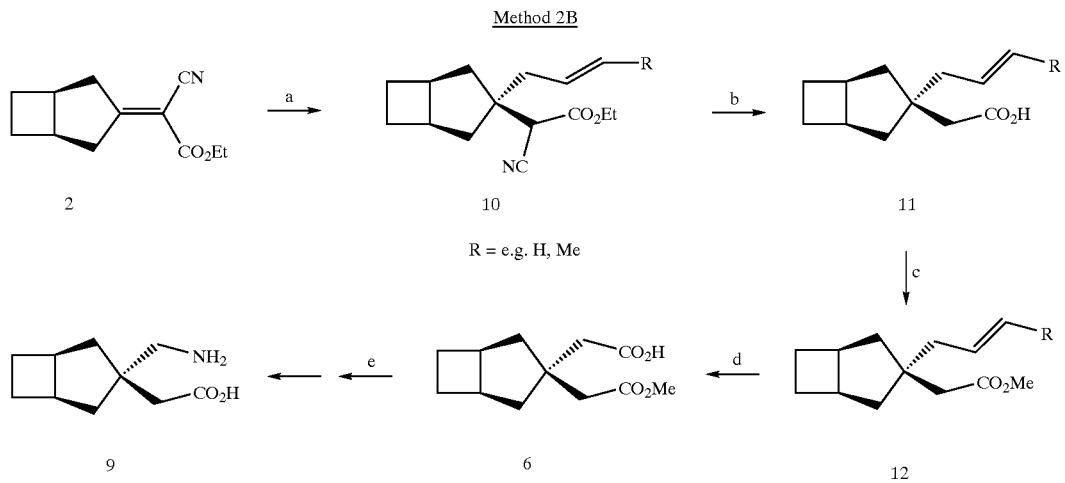

Method 2B

R = e.g. H, Me a) Cyanoester (2) is added to allylmagnesium chloride or bromide or 2-butenylmagnesium chloride in a dry solvent selected from tetrahydrofuran, 1,4-dioxane, n-heptane, toluene, diethyl ether, or tert-butyl methyl ether at a temperature from −100° C. to 110° C. to produce the addition product of formula (10);

b) Adding the product of step a) above to a mixture of a base selected from potassium hydroxide, sodium hydroxide, lithium hydroxide, or cesium hydroxide in a solvent selected from ethylene glycol, 2-methoxyethyl ether, 1,4-dioxane, or diethylene glycol and stirring the mixture at a temperature from 25° C. to 250° C. to produce the carboxylic acid of formula (11);

c) Adding the product of step b) above to a mixture of iodomethane in a solvent selected from dichloromethane, chloroform, tetrahydrofuran, toluene, or 1,4-dioxane to which a base such as 1,8-diazabicyclo[5.4.0]undec-7-ene (DBU), triethylamine, or 1,5-diazabicyclo[4.3.0]non-5-ene (DBN) was added and stirred at a temperature from −40° C. to 110° C. to produce the ester of formula (11); or adding the product of step b) above to a mixture of methanol and a concentrated acid such as sulphuric acid or hydrochloric acid at a temperature ranging from 0° C. to 100° C.; or adding the product of step b) above to trimethylsilyldiazomethane and methanol in benzene or toluene at a temperature from −40° C. to 100° C.; or adding the product of step b) above to diazomethane in a solvent such as benzene, toluene, dichloromethane, or diethyl ether at a temperature from −40° C. to 40° C.; and d) Adding the product of step c) above to a mixture of carbon tetrachloride or ethyl acetate and acetonitrile to which water, sodium periodate, and ruthenium (III) chloride were added, and stirred at a temperature from −40° C. to 80° C. to produce carboxylic acid of formula (6).

Method 2C

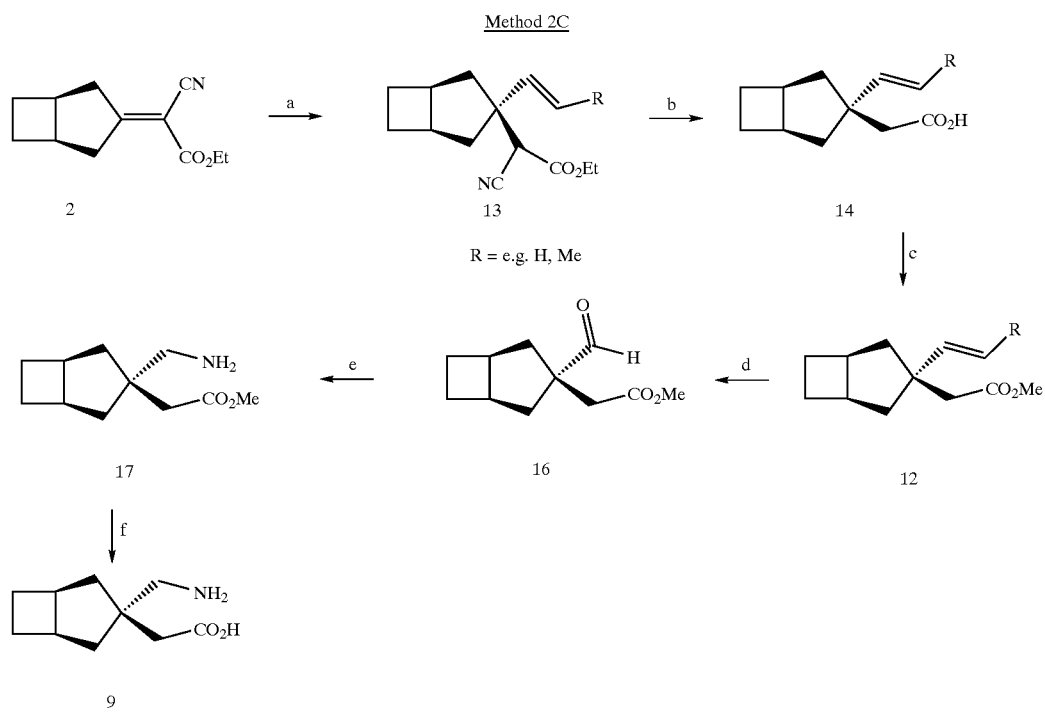

R = e.g. H, Me a) An organometallic reagent such as vinyllithium or vinylmagnesium chloride or bromide in a solvent such as tetrahydrofuiran or diethyl ether at a temperature from −100° C. to 0° C. is added to the cyanoester (2) to give (13);
b) Adding the product of step a) above to a mixture of a base selected from potassium hydroxide, sodium hydroxide, lithium hydroxide, or cesium hydroxide in a solvent selected from ethylene glycol, 2-methoxyethyl ether, 1,4-dioxane, or diethylene glycol and stirring the mixture at a temperature from 25° C. to 250° C. to produce the carboxylic acid of formula (14);
c) Adding the product of step b) above to a mixture of iodomethane in a solvent selected from dichloromethane, chloroform, tetrahydrofuran, toluene, or 1,4-dioxane to which a base such as 1,8-diazabicyclo[5.4.0]undec-7-ene (DBU), triethylamine, or 1,5-diazabicyclo[4.3.0]non-5-ene (DBN) is added and stirred at a temperature from −40° C. to 110° C. to produce the ester of formula (15); or adding the product of step b) above to a mixture of methanol and a concentrated acid such as sulphuric acid or hydrochloric acid at a temperature ranging from 0° C. to 100° C.; or adding the product of step b) above to trimethylsilyldiazomethane and methanol in benzene or toluene at a temperature from −40° C. to 100° C.; or adding the product of step b) above to diazomethane in a solvent such as benzene, toluene, dichloromethane, or diethyl ether at a temperature from −40° C. to 40° C.;
d) The product of step c) above is ozonolysed in a solvent such as chloroform or dichloromethane or methanol followed by addition of a quench such as triphenylphosphine or dimethylsulphide at a temperature from −100° C. to 0° C. to give (16);
e) The product of step d) above in a solvent such as methanol or ethanol was reacted with ammonia solution or ammonia gas followed by reduction using sodium borohydride, sodium cyanoborohydride or sodium triacetoxyborohydride, or by reduction by hydrogenation in the presence of a catalyst such as nickel, palladium, or platinum to give (17); and
f) The product of step e) above is hydrolysed using aqueous hydrochloric acid at a concentration of from 0.01 M to 12 M in the presence or absence of a solvent such as 1,4-dioxane, acetic acid, or water to produce the amino acid (9).

Method 3

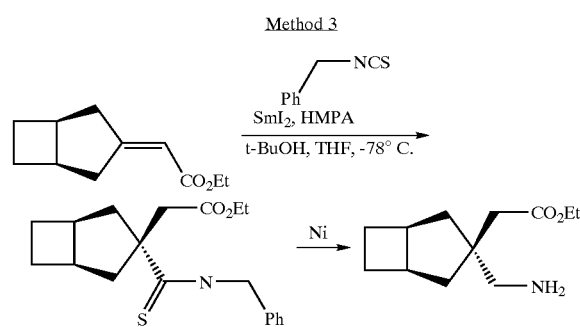

The unsaturated ester and benzyl thioisocyanate is stirred in a solvent mixture made up of tetrahydrofuran, diethyl ether, or 1,4-dioxane, a coordinating solvent such as HMPA or DMPU and an alcohol such as tert-butanol with samarium diiodide at a temperature of −100° C. to 0° C.; the resulting ester is hydrogenated in a solvent such as methanol, ethanol, ethyl acetate using a catalyst such as nickel, palladium, platinum, or rhodium at a temperature from 20° C. to 100° C. to give the amino acid.

Method 4A

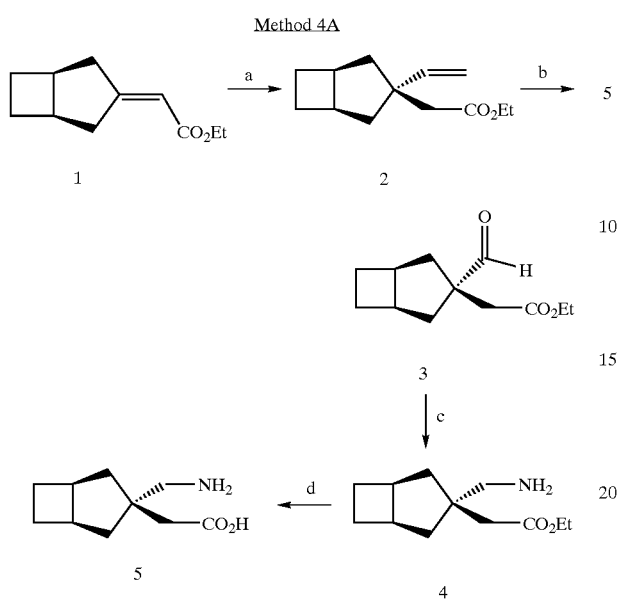

b) The product of step a) above is ozonolysed in a solvent such as chloroform or dichloromethane or methanol followed by addition of a quench such as triphenylphosphine or dimethylsulphide at a temperature from −100° C. to 0° C. to give (3);

c) The product of step b) above in a solvent such as methanol or ethanol was reacted with ammonia solution or ammonia gas followed by reduction using sodium borohydride, sodium cyanoborohydride or sodium triacetoxyborohydride, or by reduction by hydrogenation in the presence of a catalyst such as nickel, palladium, or platinum to give (4); and d) The product of step c) above is hydrolysed using aqueous hydrochloric acid at a concentration of from 0.01 M to 12 M in the presence or absence of a solvent such as 1,4-dioxane, acetic acid, or water to produce the amino acid (5).

Method 4B

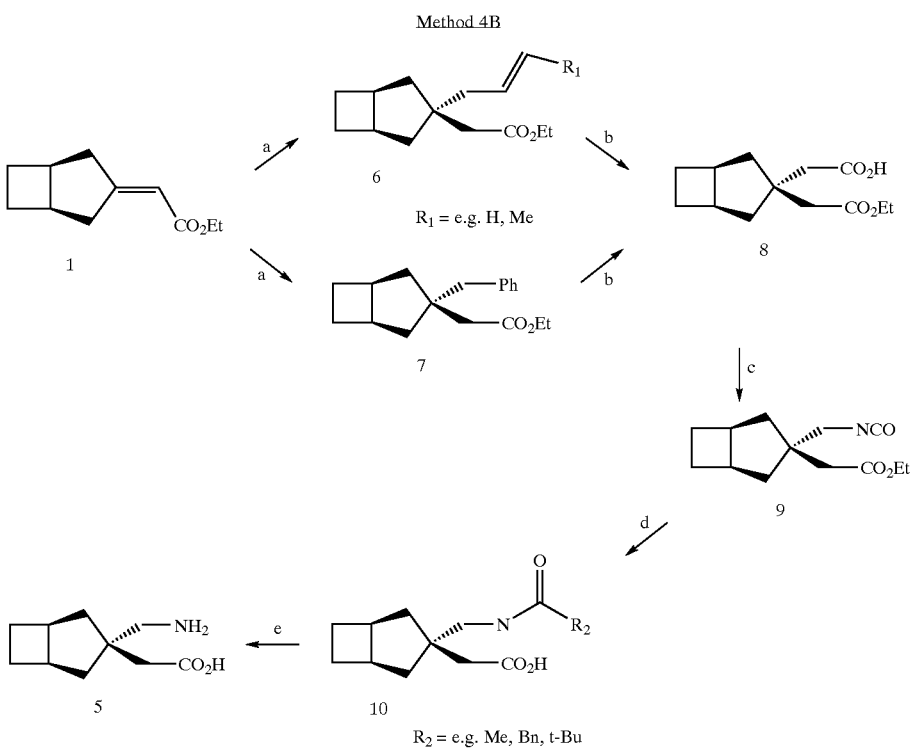

$R_1$ = e.g. H, Me $R_2$ = e.g. Me, Bn, t-Bu a) An organometallic reagent such as vinyllithium or vinylmagnesium chloride or bromide is mixed with dimethylzinc, zinc chloride, copper (I) iodide, copper (I) bromide dimethyl sulphide complex, or copper (I) cyanide in the presence of a Lewis acid such as boron trifluoride etherate or aluminium chloride in a solvent such as tetrahydrofuran or diethyl ether at a temperature from −100° C. to 0° C., and the unsaturated ester (1) is added to give addition product (2);

a) An organometallic reagent such as allylmagnesium chloride or bromide is mixed with dimethylzinc, zinc chloride, copper (I) iodide, copper (I) bromide dimethyl sulphide complex, or copper (I) cyanide in the presence of a Lewis acid such as boron trifluoride etherate or aluminium chloride in a solvent such as tetrahydrofuran or diethyl ether at a temperature from −100° C. to 0° C. and the unsaturated ester (1) is added to give addition product (6); or an organometallic reagent such as benzylmagnesium chloride or bromide is mixed with dimethylzinc, zinc chloride, copper (I) iodide, copper (I) bromide dimethyl sulphide complex, or copper (I) cyanide in the presence of a Lewis acid such as boron trifluoride etherate or aluminium chloride in a solvent such as tetrahydrofuran or diethyl ether at a temperature from −100° C. to 0° C. and the unsaturated ester (1) is added to give addition product (7);

b) Adding the product of step a) above to a mixture of carbon tetrachloride or ethyl acetate and acetonitrile to which water, sodium periodate, and ruthenium (III) chloride are added, and stirred at a temperature from −40° C. to 80° C. to produce carboxylic acid of formula (8);

c) Adding the product of step b) above to a mixture of a base selected from triethylamine or diisopropylethylamine and a solvent selected from toluene, benzene, xylenes, tetrahydrofuran, diethyl ether, or n-heptane to which diphenylphosphoryl azide (DPPA) is added and stirring at a temperature from 0° C. to 150° C. to produce the isocyanate of formula (9); or adding the product of step b) above to ethyl chloroformate or isobutyl chloroformate and a base such as triethylamine or diisopropylethylamine in tetrahydrofuiran or acetone or diethyl ether at a temperature of −40° C. to 78° C. followed by addition of sodium azide in water and tetrahydrofuran or acetone followed by addition of toluene or benzene and refluxing;

d) Adding the product of step c) above to a solvent selected from toluene, benzene, xylenes, or n-heptane to which methanol or tert-butanol was added to give (10) and then adding (10) to aqueous hydrochloric acid at a concentration of from 0.01 M to 12 M in the presence or absence of a solvent such as 1,4-dioxane, acetic acid, or water to produce the amino acid (5); or adding the product of step c) above to a solvent selected from toluene, benzene, xylenes, or n-heptane to which benzyl alcohol was added to give (10) and then hydrogenating (10) over nickel or palladium or platinum to give lactam which was then hydrolysed using aqueous hydrochloric acid at a concentration of from 0.01 M to 12 M in the presence or absence of a solvent such as 1,4-dioxane, acetic acid, or water to produce the amino acid (5).

Method 5

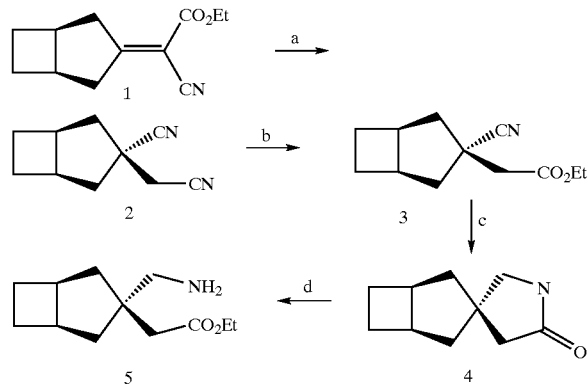

a) Compound (1) and potassium cyanide or sodium cyanide and water and ethanol or methanol are refluxed together with removal of water by, for example, use of a Dean-Stark trap to give (2);

b) The product of step a) is stirred with ethanol and toluene or benzene, and the solution is saturated with gaseous hydrochloric acid at a temperature from −30° C. to 40° C. to give (3);

c) The product of step b) above is hydrogenated in methanol, ethanol, or ethyl acetate using a catalyst such as nickel, palladium, platinum, or rhodium at a temperature from 15° C. to 60° C. to give (4); d) The product of step c) above is hydrolysed using aqueous hydrochloric acid at a concentration of from 0.01 M to 12 M in the presence or absence of a solvent such as 1,4-dioxane, acetic acid, or water to produce the amino acid (5).

Biological Examples

Several models are available to determine if the compounds of formula I–IV are effective in treating disorders of the viscera. These models include a LPS model (Eutamene H et al, *J Pharmacol Exp Ther* 2000 295 (1):162–7), a TNBS model (Diop L. et al, *Gastroenterology* 1999, 116, 4(2): A986), a IBD model (Clemett D, Markham A, *Drugs* 2000 Apr; 59(4):929–56), a pancreatic pain model (Isla A M, *Hosp Med* 2000 Jun; 61(6):386–9) and a visceral non digestive pain model (Boucher M et al, *J Urol* 2000 Jul; 164(1):203–8).

Gabapentin, which is 1-(aminomethyl)cyclohexane acetic acid, is marketed as an antiepileptic drug, and is effective in decreasing the frequency of seizures in patients.

Injections of trinitrobenzene sulfonic acid (TNBS) into the colon of the rat has been found to induce chronic colitis. Gabapentin and chemically related compounds have been shown to suppress TNBS-induced colonic hypersensitivity in a model of chronic allodynia (Diop L. et al. (1998) *Soc. Neurosci. Abstr.:* 24: 639).

The ability of the compounds of formula I–IV to treat selectively visceral disorders has been established in animal models of visceral pain for GI disorders.

In humans, GI disorders are often associated with visceral pain. In these pathologies, the visceral pain threshold is decreased indicating a visceral hypersensitivity.

Example 10

Effect of Gabapentin and the Compound of Formula Ia on TNBS-Induced Chronic Visceral Allodynia in Rats In this experimental model of colonic distension in awake rats, previous injection of TNBS into the proximal colon had lowered the visceral pain threshold.

Materials and Methods

Male Sprague-Dawley rats weighing 340–400 g are used. The animals are housed 3 per cage in a regulated environment (20±1° C., 50±5% humidity, with light 8:00 am to 8:00 pm). At day 0, under anesthesia (ketamine 80 mg/kg ip.; acepromazine 12 mg/kg ip.), the injection of TNBS (50 mg/kg in ethanol 30%), or saline (1.5 ml/kg) for control rats, is performed into the proximal colon wall (1 cm from the cecum). After the surgery, animals are individually housed in polypropylene cages and kept in a regulated environment (20±1° C., 50±5% humidity, with light 8:00 a.m. to 8:00 p.m.) during 7 days. At day 7 after TNBS administration, a balloon (5–6 cm length) is inserted by anus, and kept in position (tip of balloon 5 cm from the anus) by taping the catheter to the base of the tail. Oral administration of gabapentin or the compound of formula Ia is performed 1 h before the colonic distension cycle: the balloon is progressively inflated by steps of 5 mm Hg (0.667 kPa), from 0 to 75 mm Hg, each step of inflation lasting 30 s. Each cycle of colonic distension is controlled by a standard barostat. The threshold (mm Hg) corresponds to the pressure which produced the first abdominal contraction, and the cycle of distension is then discontinued. The colonic threshold is determined after performance of four cycles of distension on the same animal.

Data is analyzed by comparing test compound-treated groups with a TNBS only-treated group and the control group. Mean and SEM are calculated for each group. The antiallodynic activity of each oral dose of the test compound is calculated as follows:

$$\% \ Activity = \frac{A-T}{C-T} \times 100$$

where A=mean threshold of the test compound-treated group,
T=mean threshold of the TNBS only-treated group,
C=mean threshold of the control group.

The results measured in the test compound-treated groups are expressed in % inhibition of the TNBS-induced decrease in the pain threshold. Statistical significance between each group was determined by using a one-way ANOVA followed by Student's unpaired t-test; differences were considered statistically significant at p<0.05.

Results

| Effect of gabapentin: | | |
|---|---|---|
| Dose p.o. (mg/kg) | Inhibition at 1 h (%) | Number of rats |
| 100 | 14.7 ± 5.1%* | 7 |
| 300 | 48.6 ± 13.3%** | 8 |
| 500 | 64.9 ± 10.5%*** | 8 |
| 1000 | 75.2 ± 6.1%*** | 8 |

*: p < 0.05
**: p < 0.01
***: p < 0.001

The median effective dose ($ED_{50}$) of gabapentin is 321 mg/kg p.o.

| Effect of the compound of formula Ia: | | |
|---|---|---|
| Dose p.o. (mg/kg) | Inhibition at 1 h (%) | Number of rats |
| 3 | 21.7 ± 3.0%** | 7 |
| 10 | 34.2 ± 5.7%*** | 7 |
| 30 | 58.8 ± 6.2%*** | 7 |
| 60 | 90.4 ± 9.8%*** | 7 |

The $ED_{50}$ of the compound of formula Ia is 14.4 mg/kg p.o.

By the subcutaneous (s.c.) route, gabapentin is known not to modify the colonic threshold in control conditions; by contrast, in the same conditions morphine (s.c.) increased the colonic threshold in both TNBS-treated animals and in controls, suggesting a different mechanism of action. (Diop L. et al. (1998) *Soc. Neurosci. Abstr.:* 24:639).

The compound of formula Ia produced a potent antiallodynic activity in a model of visceral pain in rats, the compound being more than 20-fold more active than gabapentin in the same conditions. The respective $ED_{50}$ values are 321 mg/kg p.o. for gabapentin and 14.4 mg/kg p.o. for the compound of formula Ia Example 11

Effect of Gabapentin and the Compound of Formula Ia on LPS-Induced Rectal Hypersensitivity in Rats Intraperitoneal injection of bacterial lipo-polysaccharide (LPS) has been shown to induce rectal hyperalgesia in awake rats.

Materials and Methods

Animals are surgically prepared for electromyography: rats are anaesthetized by intraperitoneal injection of acepromazine (0.6 mg/kg) and ketamine (120 mg/kg). Three groups of three electrodes are implanted in the abdominal external oblique musculature, just superior to the inguinal ligament. Electrodes are exteriorized on the back of the neck and protected by a glass tube attached to the skin. Animals are individually housed in polypropylene cages and kept in a temperature-controlled room (21° C.). Food (UAR pellets, Epinay, France) and water are provided ad libitum.

Electromyographic recordings begin five days after surgery. The electrical activity of abdominal striated muscles is recorded with an electroencephalograph machine (Mini VIII Alvar, Paris, France) using a short time constant (0.03 s) to remove low-frequency signals (<3 Hz) and a paper speed of 3.6 cm/min. Spike bursts are recorded as an index of abdominal contractions.

Distension procedure: Rats are placed in plastic tunnels (6 cm diameter×25 cm long), where they cannot move, escape, or turn around, in order to prevent damage to the balloon. Animals are accustomed to this procedure for four days before rectal distension in order to minimize stress reactions during experiments. The balloon used for distension is an arterial embolectomy catheter (Fogarty, Edwards Laboratories Inc.). Rectal distension is performed by insertion of the balloon (2 mm diameter×2 cm long) into the rectum, at 1 cm from the anus, and catheter is fixed at the base of the tail. It is inflated progressively with tepid water by steps of 0.4 ml, from 0 to 1.2 ml, each step of inflation lasting 5 min. To detect possible leakage, the volume of water introduced in the balloon is checked by complete removal with a syringe at the end of the distension period.

Experimental protocol: Rats are injected i.p. with LPS (1 mg/kg (*Escherichia coli*, serotype O111:B4) Sigma-Aldrich chemical Co., St Louis, Mo.) or its vehicle, and rectal distension with concomitant electromyographic recording of abdominal contractions is performed 9 and 12 h after this administration. To determine the antinociceptive properties of gabapentin and the compound of formula Ia in hyperalgesia conditions, gabapentin (10 and 30 mg/kg) and the compound of formula Ia (0.01, 0.03 and 0.1 mg/kg) or the vehicle (NaCl 0.9% 0.3 ml/rat) are administered per os 1 h before rectal distension but preceded (12 h) by injection of LPS (1 mg/kg i.p.).

Drugs: All compounds were dissolved in sterile NaCl (0.9% isotonic saline) immediately before use.

Statistics: Statistical analysis of the number of abdominal contractions occurring during each period of rectal distension is performed by one-way ANOVA followed by parametric Student's unpaired t test.

Results

Effect of gabapentin: Gabapentin administered at 30 mg/kg p.o. significantly inhibits (85.3%, p<0.001) the number of abdominal contractions induced by rectal distension at 0.4 ml in LPS treated rats. At 10 mg/kg p.o., gabapentin does not produce a significant antihyperalgesic activity (24.9%).

Effect of the compound of formula Ia: After oral administration, the compound of formula Ia (0.01, 0.03 and 0.1 mg/kg po) inhibits in a dose-related manner the number of abdominal contractions induced by rectal distension at 0.4 ml after LPS treatment (FIG. 1). The $ED_{50}$ is 0.037 mg/kg p.o.

In conclusion, these results show that gabapentin and the compound of formula Ia produce an antihyperalgesic activity on LPS-induced rectal hypersensitivity, a model of visceral pain in rats. The compound of formula Ia displays a more potent antihyperalgesic activity than gabapentin. Comparison of gabapentin with the compound of formula Ia shows that the compound of formula Ia is about 500 fold more potent than gabapentin in this model of visceral pain.

The foregoing data establish that the compound of formula I–IV are effective in preventing and treating visceral pain, in particular in GI disorders such as functional bowel disorders (FBD) and inflammatory bowel diseases (IBD). In addition, such efficacy of the compound of formula Ia is observed following oral administration of the compound.

What is claimed is:

1. A method for treating gastrointestinal disorders comprising administering to a patient in need of treatment an effective amount of a compound of formula I–IV:

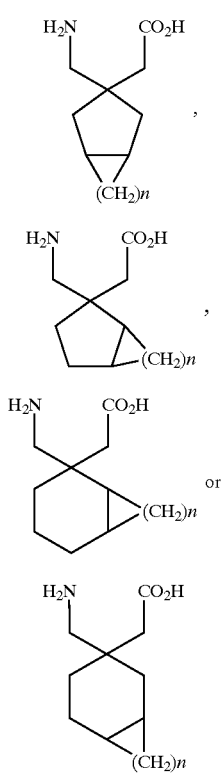

or a pharmaceutically acceptable salt thereof, wherein n is an integer of from 1 to 4.

2. The method of claim 1, wherein the compound is selected from:

(1α,6α,8β)(2-Aminomethyl-octahydro-inden-2-yl)-acetic acid,
(2-Aminomethyl-octahydro-inden-2-yl)-acetic acid,
(2-Aminomethyl-octahydro-pentalen-2-yl)-acetic acid,
(3-Aminomethyl-bicyclo[3.2.0]hept-3-yl)-acetic acid,
(1α,3α,5α)-3-aminomethyl-bicyclo[3.2.0]heptane-3-acetic acid,
(1α,5α)(3-Aminomethyl-bicyclo[3.1.0]hex-3-yl)-acetic acid,
(1α,5β)(3-Aminomethyl-bicyclo[3.2.0]hept-3-yl)-acetic acid,
(1α,5β)(2-Aminomethyl-octahydro-pentalen-2-yl)-acetic acid,
(1α,6 β)(2-Aminomethyl-octahydro-inden-2-yl)-acetic acid,
(1α,7β)(2-Aminomethyl-decahydro-azulen-2-yl)-acetic acid,
(1α,5 β)(3-Aminomethyl-bicyclo[3.1.0]hex-3-yl)-acetic acid,
(1α,5 β)(3-Aminomethyl-bicyclo[3.2.0]hept-3-yl)-acetic acid,
(1α,5β)(2-Aminomethyl-octahydro-pentalen-2-yl)-acetic acid,
(1α,6β)(2-Aminomethyl-octahydro-inden-2-yl)-acetic acid,
(1α,7β)(2-Aminomethyl-decahydro-azulen-2-yl)-acetic acid,
(1α,3α,5α)(3-Aminomethyl-bicyclo[3.2.0]hex-3-yl)-acetic acid,
(1α,3α,5α)(2-Aminomethyl-octahydro-pentalen-2-yl)-acetic acid,
(1α,6α,8α)(2-Aminomethyl-octahydro-inden-2-yl)-acetic acid,
(1α,7α,9β)(2-Aminomethyl-decahydro-azulen-2-yl)-acetic acid,
(1α,3α,5α)(3-Aminomethyl-bicyclo[3.1.0]hex-3-yl)-acetic acid,
(1α,3β,5α)(3-Aminomethyl-bicyclo[3.2.0]hept-3-yl)-acetic acid,
(1α,3α,5α)(2-Aminomethyl-octahydro-pentalen-2-yl)-acetic acid,
(1α,6α,8α)(2-Aminomethyl-octahydro-inden-2-yl)-acetic acid,
(1α,7α,9α)(2-Aminomethyl-decahydro-azulen-2-yl)-acetic acid,
((1R,3R,6R)-3-Aminomethyl-bicyclo[4.1.0]hept-3-yl)-acetic acid,
((1R,3 S,6R)-3-Aminomethyl-bicyclo[4.1.0]hept-3-yl)-acetic acid,
((1S,3S,6S)-3-Aminomethyl-bicyclo[4.1.0]hept-3-yl)-acetic acid,
((1 S,3R,6S)-3-Aminomethyl-bicyclo[4.1.0]hept-3-yl)-acetic acid,
((1R,3R,6S)-3-Aminomethyl-bicyclo[4.2.0]oct-3-yl)-acetic acid,
((1R,3S,6S)-3-Aminomethyl-bicyclo[4.2.0]oct-3-yl)-acetic acid,
((1S,3S,6R)-3-Aminomethyl-bicyclo[4.2.0]oct-3-yl)-acetic acid,
((1S,3R,6R)-3-Aminomethyl-bicyclo[4.2.0]oct-3-yl)-acetic acid,
((3αR,5R,7αS)-5-Aminomethyl-octahydro-inden-5-yl)-acetic acid,
((3αR,5S,7αS)-5-Aminomethyl-octahydro-inden-5-yl)-acetic acid,
((3αS,5S,7αR)-5-Aminomethyl-octahydro-inden-5-yl)-acetic acid,
((3αS,5R,7αR)-5-Aminomethyl-octahydro-inden-5-yl)-acetic acid,
((2R,4αS,8αR)-2-Aminomethyl-decahydro-naphthalen-2-yl)-acetic acid,
((2S,4αS,8αR)-2-Aminomethyl-decahydro-naphthalen-2-yl)-acetic acid,
((2S,4αR,8αS)-2-Aminomethyl-decahydro-naphthalen-2-yl)-acetic acid,
((2R,4αR,8αS)-2-Aminomethyl-decahydro-naphthalen-2-yl)-acetic acid,
((2R,4αS,9αR)-2-Aminomethyl-decahydro-benzocyclohepten-2-yl)-acetic acid, ((2S,4αS,9αR)-2-Aminomethyl-decahydro-benzocyclohepten-2-yl)-acetic acid,
((2S,4αR,9αS)-2-Aminomethyl-decahydro-benzocyclohepten-2-yl)-acetic acid,
((2R,4αR,9αS)-2-Aminomethyl-decahydro-benzocyclohepten-2-yl)-acetic acid,
((1R,3R,6S)-3-Aminomethyl-bicyclo[4.1.0]hept-3-yl)-acetic acid,
((1R,3 S,6S)-3-Aminomethyl-bicyclo[4.1.0]hept-3-yl)-acetic acid,
((1S,3S,6R)-3-Aminomethyl-bicyclo[4.1.0] hept-3-yl)-acetic acid,
((1S,3R,6R)-3-Aminomethyl-bicyclo[4.1.0]hept-3-yl)-acetic acid,
((1R,3R,6R)-3-Aminomethyl-bicyclo[4.2.0]oct-3-yl)-acetic acid,
((1R,3S,6R)-3-Aminomethyl-bicyclo[4.2.0]oct-3-yl)-acetic acid,
((1S,3S,6S)-3-Aminomethyl-bicyclo[4.2.0]oct-3-yl)-acetic acid,
((1S,3R,6S)-3-Aminomethyl-bicyclo[4.2.0]oct-3-yl)-acetic acid,
((3αR,5R,7αR)-5-Aminomethyl-octahydro-inden-5-yl)-acetic acid,
((3αR,5S,7αR)-5-Aminomethyl-octahydro-inden-5-yl)-acetic acid,
((3αS,5S,7αS)-5-Aminomethyl-octahydro-inden-5-yl)-acetic acid,
((3αS,5R,7αS)-5-Aminomethyl-octahydro-inden-5-yl)-acetic acid,
((2R,4αR,8αR)-2-Aminomethyl-decahydro-naphthalen-2-yl)-acetic acid,
((2S,4αS,8αR)-2-Aminomethyl-decahydro-naphthalen-2-yl)-acetic acid,
((2S,4αR,8αS)-2-Aminomethyl-decahydro-naphthalen-2-yl)-acetic acid,
((2R,4αS,8αS)-2-Aminomethyl-decahydro-naphthalen-2-yl)-acetic acid,
((2R,4αR,9αR)-2-Aminomethyl-decahydro-benzocyclohepten-2-yl)-acetic acid,
((2S,4αR,9αR)-2-Aminomethyl-decahydro-benzocyclohepten-2-yl)-acetic acid,
((2S,4αS,9αS)-2-Aminomethyl-decahydro-benzocyclohepten-2-yl)-acetic acid, and
((2R,4αS,9αS)-2-Aminomethyl-decahydro-benzocyclohepten-2-yl)-acetic acid,
or a pharmaceutically acceptable salt thereof.

3. The method according to claim 2, wherein the compound is the compound of formula I or a pharmaceutically acceptable salt thereof.

4. A method for treating gastrointestinal disorders comprising administering to a patient in need of treatment an effective amount of (1α,3α,5α)-3-aminomethyl-bicyclo[3.2.0]heptane-3-acetic acid or a pharmaceutically acceptable salt thereof.

5. The method according to any one of claims 1, 2, 3 and 4, wherein the disorder is functional bowel disorder or inflammatory bowel disease.

6. The method according to claim 5, wherein the functional bowel disorder is gastro-esophageal reflux, dyspepsia, irritable bowel syndrome or functional abdominal pain syndrome.

7. The method according to claim 5, wherein the inflammatory bowel disease is Crohn's disease, ileitis or ulcerative colitis.

8. A method for treating irritable bowel syndrome comprising administering to a patient in need of treatment an effective amount of a compound of formula I–IV:

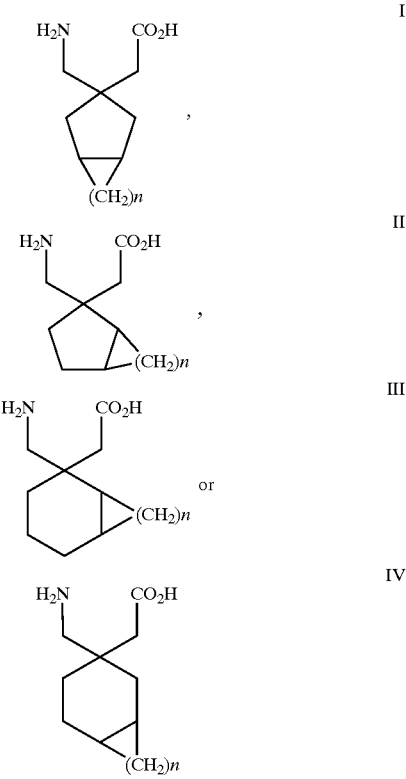

or a pharmaceutically acceptable salt thereof, wherein n is an integer of from 1 to 4.

9. The method of claim 8, wherein the compound is selected from:
(1α,6α,8β)(2-Aminomethyl-octahydro-inden-2-yl)-acetic acid,
(2-Aminomethyl-octahydro-inden-2-yl)-acetic acid,
(2-Aminomethyl-octahydro-pentalen-2-yl)-acetic acid,
(3-Aminomethyl-bicyclo[3.2.0]hept-3-yl)-acetic acid,
(1α,3α,5α)-3-aminomethyl-bicyclo[3.2.0]heptane-3-acetic acid,
(1α,5α)(3-Aminomethyl-bicyclo[3.1.0]hex-3-yl)-acetic acid,
(1α,5β)(3-Aminomethyl-bicyclo[3.2.0]hept-3-yl)-acetic acid,
(1α,5β)(2-Aminomethyl-octahydro-pentalen-2-yl)-acetic acid,
(1α,6 β)(2-Aminomethyl-octahydro-inden-2-yl)-acetic acid,
(1α,7β)(2-Aminomethyl-decahydro-azulen-2-yl)-acetic acid,
(1α,5 β)(3-Aminomethyl-bicyclo[3.1.0]hex-3-yl)-acetic acid,
(1α,5 β)(3-Aminomethyl-bicyclo[3.2.0]hept-3-yl)-acetic acid,
(1α,5β)(2-Aminomethyl-octahydro-pentalen-2-yl)-acetic acid,
(1α,6β)(2-Aminomethyl-octahydro-inden-2-yl)-acetic acid,
(1α,7β)(2-Aminomethyl-decahydro-azulen-2-yl)-acetic acid, (1α,3α,5α)(3-Aminomethyl-bicyclo[3.2.0]hex-3-yl)-acetic acid,
(1α,3α,5α)(2-Aminomethyl-octahydro-pentalen-2-yl)-acetic acid,
(1α,6α,8α)(2-Aminomethyl-octahydro-inden-2-yl)-acetic acid,
(1α,7α,9β)(2-Aminomethyl-decahydro-azulen-2-yl)-acetic acid,
(1α,3α,5α)(3-Aminomethyl-bicyclo[3.1.0]hex-3-yl)-acetic acid,
(1α,3β,5α)(3-Aminomethyl-bicyclo[3.2.0]hept-3-yl)-acetic acid,
(1α,3α,5α)(2-Aminomethyl-octahydro-pentalen-2-yl)-acetic acid,
(1α,6α,8α)(2-Aminomethyl-octahydro-inden-2-yl)-acetic acid,
(1α,7α,9α)(2-Aminomethyl-decahydro-azulen-2-yl)-acetic acid,
((1R,3R,6R)-3-Aminomethyl-bicyclo[4.1.0]hept-3-yl)-acetic acid,
((1R,3 S,6R)-3-Aminomethyl-bicyclo[4.1.0]hept-3-yl)-acetic acid,
((1S,3S,6S)-3-Aminomethyl-bicyclo[4.1.0]hept-3-yl)-acetic acid,
((1 S,3R,6S)-3-Aminomethyl-bicyclo[4.1.0]hept-3-yl)-acetic acid,
((1R,3R,6S)-3-Aminomethyl-bicyclo[4.2.0]oct-3-yl)-acetic acid,
((1R,3S,6S)-3-Aminomethyl-bicyclo[4.2.0]oct-3-yl)-acetic acid,
((1S,3S,6R)-3-Aminomethyl-bicyclo[4.2.0]oct-3-yl)-acetic acid,
((1S,3R,6R)-3-Aminomethyl-bicyclo[4.2.0]oct-3-yl)-acetic acid,
((3αR,5R,7αS)-5-Aminomethyl-octahydro-inden-5-yl)-acetic acid,
((3αR,5S,7αS)-5-Aminomethyl-octahydro-inden-5-yl)-acetic acid,
((3αS,5S,7αR)-5-Aminomethyl-octahydro-inden-5-yl)-acetic acid,
((3αS,5R,7αR)-5-Aminomethyl-octahydro-inden-5-yl)-acetic acid,
((2R,4αS,8αR)-2-Aminomethyl-decahydro-naphthalen-2-yl)-acetic acid,
((2S,4αS,8αR)-2-Aminomethyl-decahydro-naphthalen-2-yl)-acetic acid,
((2S,4αR,8αS)-2-Aminomethyl-decahydro-naphthalen-2-yl)-acetic acid,
((2R,4αR,8αS)-2-Aminomethyl-decahydro-naphthalen-2-yl)-acetic acid,
((2R,4αS,9αR)-2-Aminomethyl-decahydro-benzocyclohepten-2-yl)-acetic acid,
((2S,4αS,9αR)-2-Aminomethyl-decahydro-benzocyclohepten-2-yl)-acetic acid,
((2S,4αR,9αS)-2-Aminomethyl-decahydro-benzocyclohepten-2-yl)-acetic acid,
((2R,4αR,9αS)-2-Aminomethyl-decahydro-benzocyclohepten-2-yl)-acetic acid,
((1R,3R,6S)-3-Aminomethyl-bicyclo[4.1.0]hept-3-yl)-acetic acid,
((1R,3S,6S)-3-Aminomethyl-bicyclo[4.1.0]hept-3-yl)-acetic acid,
((1S,3S,6R)-3-Aminomethyl-bicyclo[4.1.0] hept-3-yl)-acetic acid,
((1S,3R,6R)-3-Aminomethyl-bicyclo[4.1.0]hept-3-yl)-acetic acid,
((1R,3R,6R)-3-Aminomethyl-bicyclo[4.2.0]oct-3-yl)-acetic acid,
((1R,3S,6R)-3-Aminomethyl-bicyclo[4.2.0]oct-3-yl)-acetic acid,
((1S,3S,6S)-3-Aminomethyl-bicyclo[4.2.0]oct-3-yl)-acetic acid,
((1S,3R,6S)-3-Aminomethyl-bicyclo[4.2.0]oct-3-yl)-acetic acid,
((3αR,5R,7αR)-5-Aminomethyl-octahydro-inden-5-yl)-acetic acid,
((3αR,5S,7αR)-5-Aminomethyl-octahydro-inden-5-yl)-acetic acid,
((3αS,5S,7αS)-5-Aminomethyl-octahydro-inden-5-yl)-acetic acid,
((3αS,5R,7αS)-5-Aminomethyl-octahydro-inden-5-yl)-acetic acid,
((2R,4αR,8αR)-2-Aminomethyl-decahydro-naphthalen-2-yl)-acetic acid,
((2S,4αS,8αR)-2-Aminomethyl-decahydro-naphthalen-2-yl)-acetic acid,
((2S,4αR,8αS)-2-Aminomethyl-decahydro-naphthalen-2-yl)-acetic acid,
((2R,4αS,8αS)-2-Aminomethyl-decahydro-naphthalen-2-yl)-acetic acid,
((2R,4αR,9αR)-2-Aminomethyl-decahydro-benzocyclohepten-2-yl)-acetic acid,
((2S,4αR,9αR)-2-Aminomethyl-decahydro-benzocyclohepten-2-yl)-acetic acid,
((2S,4αS,9αS)-2-Aminomethyl-decahydro-benzocyclohepten-2-yl)-acetic acid, and
((2R,4αS,9αS)-2-Aminomethyl-decahydro-benzocyclohepten-2-yl)-acetic acid,
or a pharmaceutically acceptable salt thereof.

10. The method according to claim 8, wherein the compound is the compound of formula I or a pharmaceutically acceptable salt thereof.

11. A method for treating irritable bowel syndrome comprising administering to a patient in need of treatments effective amount of (1α,3α,5α)-3-aminomethyl-bicyclo[3.2.0]heptane-3-acetic acid or a pharmaceutically acceptable salt thereof.

* * * * *